(12) United States Patent
Michoud

(10) Patent No.: US 7,485,752 B2
(45) Date of Patent: Feb. 3, 2009

(54) DIACYLGLYCEROL ACYLTRANSFERASE INHIBITORS

(75) Inventor: Christophe Michoud, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 63 days.

(21) Appl. No.: 11/429,137

(22) Filed: May 5, 2006

(65) Prior Publication Data

US 2006/0258740 A1    Nov. 16, 2006

Related U.S. Application Data

(60) Provisional application No. 60/679,521, filed on May 10, 2005.

(51) Int. Cl.
C07C 243/14  (2006.01)
A61K 31/16  (2006.01)

(52) U.S. Cl. .................. 564/149; 514/432; 514/448; 514/451; 514/461; 514/614; 514/615; 514/616; 549/13; 549/72; 549/425; 549/487; 564/148; 564/150

(58) Field of Classification Search .......... 564/149, 564/148, 150; 514/615, 616, 614, 432, 448, 514/451, 461; 549/13, 72, 425, 487
See application file for complete search history.

(56) References Cited

U.S. PATENT DOCUMENTS

| 3,278,596 | A | * | 10/1966 | Pursglove | .......... 564/134 |
| 3,884,874 | A | * | 5/1975 | Rosenberger et al. | ....... 524/191 |
| 5,358,966 | A | * | 10/1994 | James et al. | .......... 514/615 |
| 5,424,333 | A | | 6/1995 | Wing et al. | |
| 6,013,836 | A | | 1/2000 | Hsu et al. | |

FOREIGN PATENT DOCUMENTS

| EP | 0 347 216 A2 | 12/1989 |
| EP | 1219716 | 7/2002 |
| JP | 2004067635 | 3/2004 |
| WO | WO2004047755 | 6/2004 |

OTHER PUBLICATIONS

Magedov et al, Synthesis, pp. 845-848, 1991.*
Gottschling, Dirk et al *aNGEWANDTE Chemie, Internat'l Ed*, 41(16) 3007-3011 (2002) XP002385990.
Wang et al, *Heteroatom Chem*, 14(4) 293-297 (2003( XP002385991.
Mukherjee, R., *Jour. of the Chem. Soc. Chem. Comm*, (18), 1113-1114 XP008065519 (1971).
Takamizawa, A. et al, *Chem. & Pharm. Bulletin*, 23(5) 948-954 (1975) XP008065520.
Subauste and Burant, Current Drug Targets—Immune, Endocrine & Metabolic Disorders (2003) 3, 263-270.
Mayorek et al, European Journal of Biochemistry (1989) 182, 395-400.
Farese et al, Current Opinions in Lipidology (2000) 11, 229-234.
Coleman et al, Journal of Molecular Biology (1978) 253, 7256-7261.
Yu et al, Journal of Molecular Biology (2002) 277, 50876-50884.
Colman, Methods in Enzymology (1992) 209, 98-104.
Owen et al, Biochemical Journal (1997) 323 (pt 1), 17-21.
Waterman et al, Journal of Lipid Research (2002) 43, 1555-1156.
Shelness and Sellers, Current Opinions in Lipidology (2001) 12, 151-157.
Cases et al, Proceedings of the National Academy of Science, USA (1998) 95, 13018-13023.
Lardizabal et al, Journal of Biological Chemistry (2001) 276, 38862-38869.
Cases et al, Journal of Biological Chemistry (2001) 276, 38870-38876.
Smith et al, Nature Genetics (2000) 25, 87-90.
Lehner and Kuksis, Progress in Lipid Research (1996) 35, 169-210.
Chen and Farese, Trends in Cardiovascular Medicine (2000) 10, 188-192.
Chen and Farese, Current Opinions in Clinical Nutrition and Metabolic Care (2002) 5, 359-363.
Chen et al, Journal of Clinical Investigation (2002) 109, 1049-1055.
Buhman et al, Journal of Biological Chemistry (2002) 277, 25474-25479.
Kahn, Nature Genetics (2000) 25, 6-7.
Yanovski and Yanovski, New England Journal of Medicine (2002) 346, 591-602.
Lewis et al, Endocrine Reviews (2002) 23, 201.
Brazil, Nature Reviews Drug Discovery (2002) 1, 408.
Malloy and Kane, Advances in Internal Medicine (2001) 47, 111.
Yu and Ginsberg, Annals of Medicine (2004) 36, 252-261.
Burrows et al, 26th National Medicinal Chemistry Symposium (1998) poster C-22.
Tabata et al, Phytochemistry (1997) 46, 683-687.
Casaschi et al, Journal of Nutrition (2004) 134, 1340-1346.

(Continued)

*Primary Examiner*—Shailendra Kumar
(74) *Attorney, Agent, or Firm*—George W. Johnston; Dennis P. Tramaloni; Samuel H. Megerditchian

(57) ABSTRACT

Provided herein are compounds of the formula (I):

$$R_1-Y-\overset{O}{\underset{}{C}}-\underset{R_2}{N}-N-\overset{}{\underset{O}{C}}-R_3$$

as well as pharmaceutically acceptable salts thereof, wherein the substituents are as those disclosed in the specification. These compounds, and the pharmaceutical compositions containing them, are useful for the treatment of diseases such as, for example, obesity, type II diabetes mellitus and metabolic syndrome.

19 Claims, No Drawings

OTHER PUBLICATIONS

Kurogi et al, Journal of Medicinal Chemistry (1996) 39, 1433-1437.
Goto, et al, Chemistry and Pharmaceutical Bulletin (1996) 44, 547-551.
Ikeda, et al, Thirteenth International Symposium on Athersclerosis (2003), abstract 2P-0401.
Colman et al, Biochimica et Biophysica Acta (1992) 1125, 203-9.
Mayorek and Bar-Tana, Journal of Biological Chemistry (1985) 260, 6528-6532.
Noriko et al, (Journal of Antibiotics (1999) 52, 815-826.
Tomoda et al, Journal of Antibiotics (1995) 48, 942-7.
Chung et al, Planta Medica (2004) 70, 258-260.
Lee et al, Planta Medica (2004) 70, 197-200.
Lee et al, Journal of Antibiotics (2003) 56, 967-969.
Ko et al, Archives of Pharmaceutical Research (2002) 25, 446-448.
Zhu et al, Atherosclerosis (2002) 164, 221-228.
Ko, et al, Planta Medica (2002) 68, 1131-1133.
E. Von Arx, M. Faupel and M Brugger, *J. Chromatography*, 1976, 220, 224-228.

* cited by examiner

DIACYLGLYCEROL ACYLTRANSFERASE INHIBITORS

PRIORITY TO RELATED APPLICATIONS

This application claims the benefit of U.S. Provisional Application No. 60/679,521, filed May 10, 2005, which is hereby incorporated by reference in its entirety.

FIELD OF THE INVENTION

The invention relates to inhibitors of diacylglycerol acyltransferase. The inhibitors include, for example, phenyl acrylic and propionic acid derivatives and are useful for the treatment of diseases such as obesity, type II diabetes mellitus and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver and adipocytes. Triglycerides or triacylglycerols support the major functions of dietary fat absorption, packaging of newly synthesized fatty acids, and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT were cloned and designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Further, although both enzymes are widely expressed, differences exist in the relative abundance of DGAT1 and DGAT2 expression in various tissues.

The gene encoding mouse DGAT1 has been used to create DGAT knock-out mice. These mice, although unable to express a functional DGAT enzyme (Dgat–/– mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat–/– mice are resistant to diet-induced obesity and remain lean. When fed a high fat diet, Dgat–/– mice maintain weights comparable to mice fed a diet with regular fat content. Dgat–/– mice also have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat–/– mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, have been implicated in the pathogenesis of a variety of diseases risk. These include obesity, insulin resistance syndrome, type II diabetes, metabolic syndrome (syndrome X) and coronary heart disease (see Kahn, Nature Genetics (2000) 25, 6-7, Yanovski and Yanovski, New England Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets—Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), and substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133).

A need exits in the art, however, for additional DGAT inhibitors that have efficacy for the treatment of metabolic disorders such as, for example, obesity, type II diabetes mellitus and metabolic syndrome. Further, a need exists in the art for DGAT inhibitors having $IC_{50}$ values less than about 1 µM.

SUMMARY OF THE INVENTION

In an embodiment of the present invention, a compound of the formula (I) is provided:

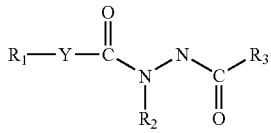

In another embodiment of the present invention, a method for the treatment of obesity, type II diabetes or metabolic syndrome in a patient in need thereof is provided, which comprises administering to said patient a therapeutically effective amount of a compound of the formula (I).

In a further embodiment of the present invention, a pharmaceutical composition is provided having a therapeutically effective amount of a compound or a pharmaceutically acceptable salt or ester thereof according to the compound of formula (I) above, and a pharmaceutically acceptable carrier.

DETAILED DESCRIPTION OF THE INVENTION

The present invention pertains to DGAT inhibitors that are derivatives of, for example, phenyl acrylic and propionic acid. In a preferred embodiment, the invention provides compounds of the formula:

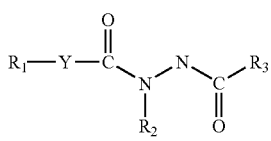

as well as pharmaceutically acceptable salts thereof. Preferably, Y is $(C_1-C_6)$ alkyl or $(C_1-C_6)$ alkyl substituted with aryl, more preferably Y is CH=CH, $(CH_2)_n$, or —CH(Ar)CH$_2$, wherein n is 1 or 2; $R_1$ is substituted or unsubstituted aryl or

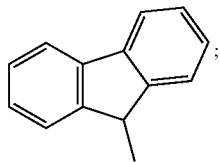

$R_2$ is $(C_1-C_6)$ alkyl, preferably cyclomethoxy cyclobutylmethoxy group; $R_3$ is unsubstituted aryl, substituted aryl with a group independently selected from the group consisting of halogen, $(C_1-C_6)$ alkyl, and —O(CH$_2$)$_m$OCH$_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocycyl substituted with $(C_1-C_6)$ alkyl, or substituted or unsubstituted 5-10-membered cycloalkyl ring; and m is 0, 1, 2 or 3. Preferably, $R_3$ is phenyl.

In another preferred embodiment, $R_1$ is:

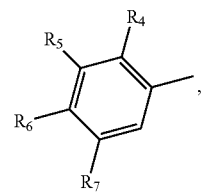

wherein $R_4$ is H, $(C_1-C_6)$ alkyl, unsubstituted aryl, aryl which is mono-, di- or tri-substituted with a group independently selected from the group consisting of halogen, $(C_1-C_6)$ alkyl, $(C_1-C_6)$ alkoxy, —O(CH)(CH$_3$)$_2$, —CF$_3$, —O(CH$_2$)$_m$CH$_3$, —OCF$_3$, —SCH$_3$, —CH(CH$_3$)$_2$, —CN, —SO$_2$CH$_3$, —NO$_2$, and —(CH)$_2$Ar, O-phenyl, —O(CH$_2$)$_m$CH$_3$, or unsubstituted or substituted 4-10 membered cycloalkyl ring attached to the aryl ring by oxygen; $R_5$, $R_6$, $R_7$ independently of each other are H, halogen, phenyl or $(C_1-C_6)$ alkyl; and m is 0, 1, 2 or 3.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl)hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl(n-butyl, isobutyl or tertiary-butyl). It will be appreciated therefore that the term "lower alkyl" as used herein includes, for example, lower alkyl (branched or unbranched), lower alkenyl (branched or unbranched), lower alkynyl (branched or unbranched), cycloloweralkyl, cycloloweralkenyl and cycloloweralkynyl.

As used herein, the term "aryl" means, for example, a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters(e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific Examples detailed below.

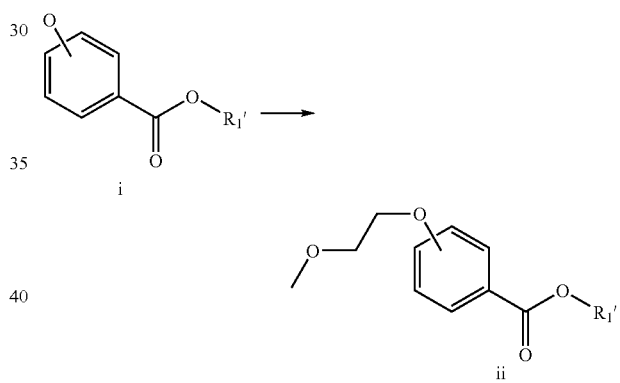

Scheme 1

As shown in Scheme 1, hydroxy-substituted benzoate esters i can be alkylated with 2-bromoethyl methyl ether by heating in the presence of potassium carbonate to give the alkoxy-ether substituted benzoate esters ii, where $R_1'$ is lower alkyl.

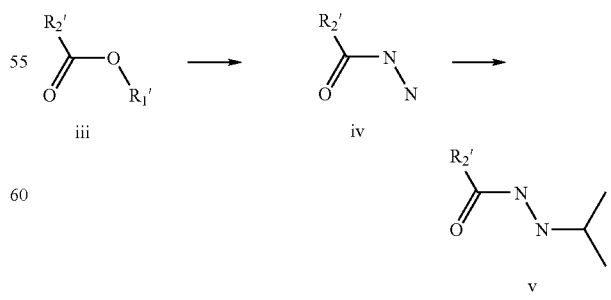

Scheme 2

As shown in scheme 2, esters iii, where $R_1'$ is lower alkyl and $R_2'$ is aryl, substituted aryl, heteroaryl, substituted heteroaryl, cycloalkyl or cycloheteroalkyl can be treated with hydrazine monohydrate in an appropriate solvent with heating to yield hydrazide iv.

Hydrazide iv can be dissolved in acetone, heated and then concentrated to dryness. The residue can be dissolved in TFA and treated with triethylsilane, with warming, to yield alkyl hydrazide v, where $R_2'$ is aryl, substituted aryl, heteroaryl, substituted heteroaryl, cycloalkyl or cycloheteroalkyl.

priate solvent, typically THF, to yield viii, where $R_3'$ is H, halogen, lower alkyl, nitro, alkoxy, thioalkoxy, haloalkoxy, lower alkyl carboxylate, or alkyl sulfonyl and $R_1'$ is lower alkyl.

The phenyl-acrylate ester viii can be hydrolyzed by heating with a strong base, typically sodium hydroxide in an aqueous/organic mixed solvent, typically THF to give the phenyl-acrylic acid viii, where $R_3'$ is H, halogen, lower alkyl, nitro, alkoxy, thioalkoxy, haloalkoxy, lower alkyl carboxylate, or alkyl sulfonyl.

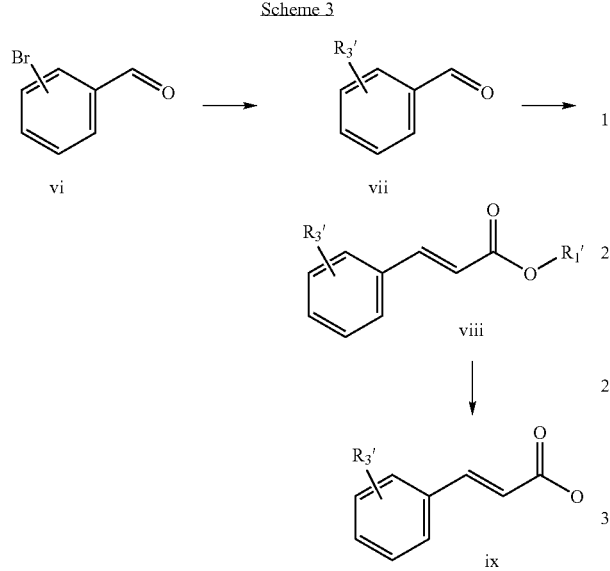

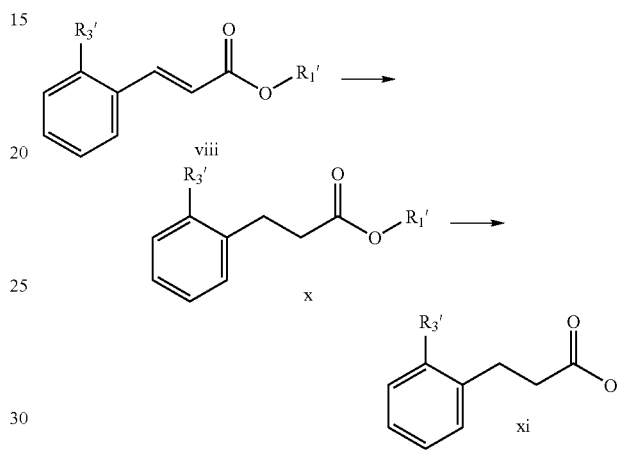

As shown in Scheme 3, using standard palladium catalyzed "cross coupling" procedures, a bromo-benzaldehyde vi can be heated, preferably in a microwave reactor, with a commercially available substituted phenylboronic acid in the presence of a base, typically an aqueous solution of sodium carbonate, in an appropriate solvent, typically, DME, DMF or toluene, with a catalytic amount of palladium, typically Pd[PPh$_3$]$_4$, to yield vii, where $R_3'$ is H, halogen, lower alkyl, nitro, alkoxy, thioalkoxy, haloalkoxy, lower alkyl carboxylate, or alkyl sulfonyl.

Substituted benzaldehyde vii can be treated with a solution of triethylphosphonoacetate and sodium hydride in an appro- As shown in scheme 4, phenyl-acrylate ester viii can be hydrogenated in an appropriate solvent with a catalyst, typically 10% palladium on carbon, under an atmosphere of hydrogen, typically 50 psi, to give substituted phenyl-propionate ester x, where $R_3'$ is H, halogen, lower alkyl, nitro, alkoxy, thioalkoxy, haloalkoxy, lower alkyl carboxylate, or alkyl sulfonyl and $R_1'$ is lower alkyl. Phenyl-propionate ester x can be hydrolyzed by heating with a strong base, typically sodium hydroxide in an aqueous/organic mixed solvent, typically THF to give the phenyl-propionic acid xi, where $R_3'$ is H, halogen, lower alkyl, nitro, alkoxy, thioalkoxy, haloalkoxy, lower alkyl carboxylate, or alkyl sulfonyl.

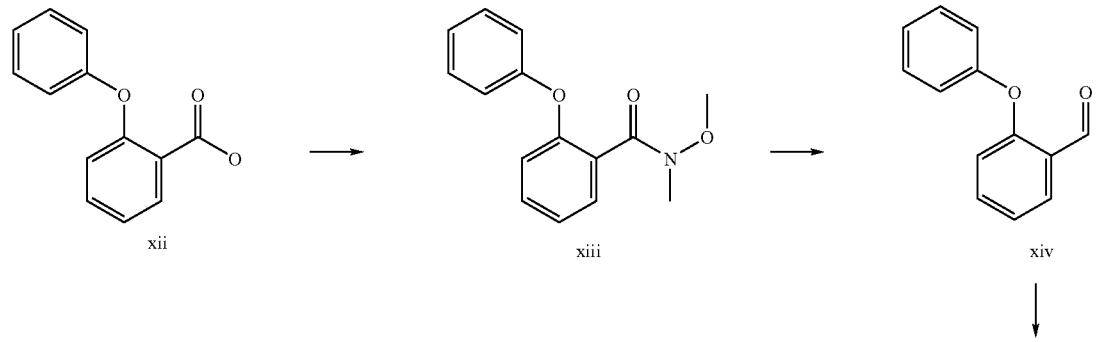

-continued

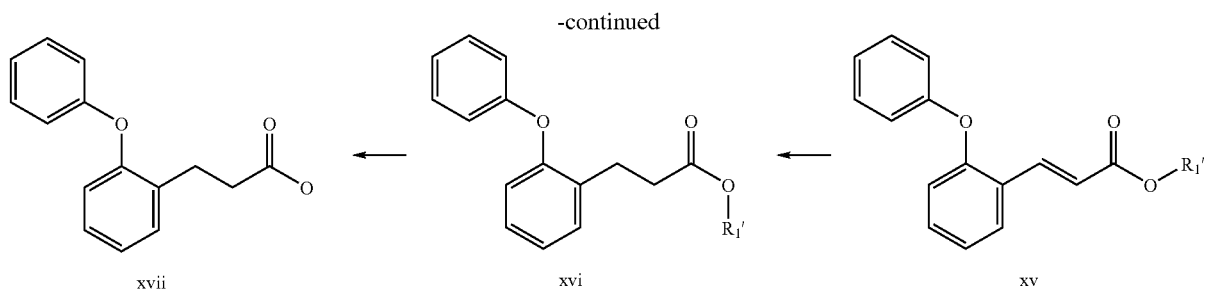

As shown in Scheme 5, a solution of 2-phenoxybenzoic acid xii and N,O-dimethylhydroxylamine hydrochloride in an appropriate solvent, typically DMF, with a base, typically triethylamine, can be reacted with a suitable coupling reagent, typically HBTU, to form the "Weinreb" amide xiii.

Amide xiii can be reduced with lithium aluminum hydride in THF to afford aldehyde xiv. Without purification, aldehyde xiv can be treated with a solution of triethylphosphonoacetate and sodium hydride in an appropriate solvent, typically THF, to yield xv, where $R_1'$ is lower alkyl.

Phenyl-acrylate ester xv can be hydrogenated in an appropriate solvent with a catalyst, typically 10% palladium on carbon, under an atmosphere of hydrogen, typically 50 psi, to give substituted phenyl-propionate ester xvi, where $R_1'$ is lower alkyl. Phenyl-propionate ester xvi can be hydrolyzed by heating with a strong base, typically lithium hydroxide in an aqueous/organic mixed solvent, typically THF, to give the o-phenoxy-phenyl-propionic acid xvii.

Scheme 6

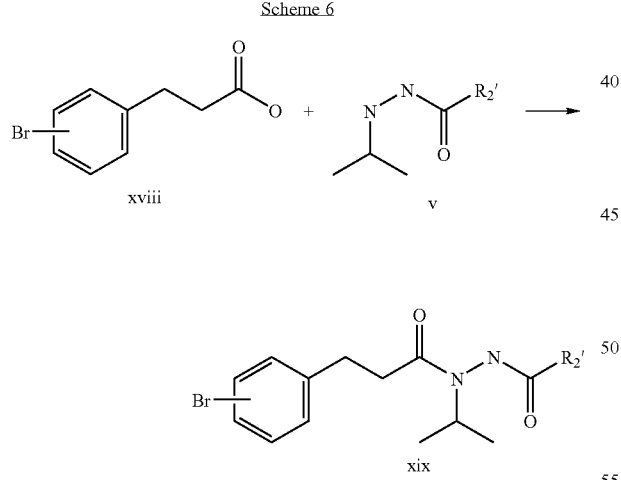

As shown in Scheme 6, a bromo-phenyl-propionic acid xviii can be used to acylate a hydrazide v from Scheme 2, where $R_2'$ is aryl, substituted aryl, heteroaryl, substituted heteroaryl, cycloalkyl or cycloheteroalkyl. Various standard amide bond forming conditions, as practiced by those skilled in the art, may be used. Typically xviii and hydrazide v, in an appropriate solvent, may be treated with a base, such as triethyl amine, and PyBroP or EDCI and HOBT to yield acyl hydrazide xix, where $R_2'$ is aryl, substituted aryl, substituted heteroaryl, cycloalkyl or cycloheteroalkyl.

Scheme 7

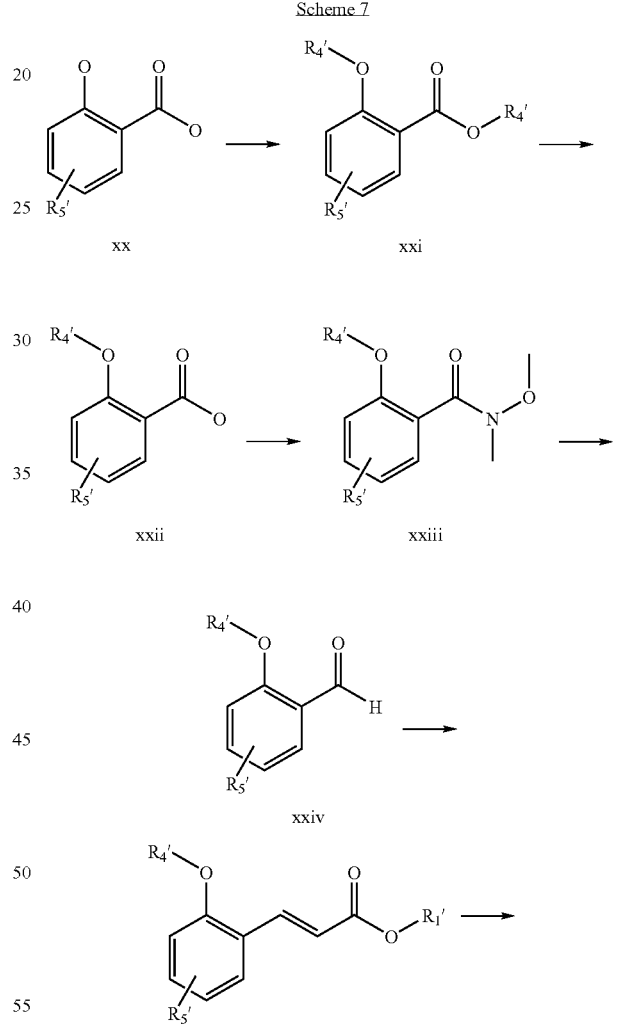

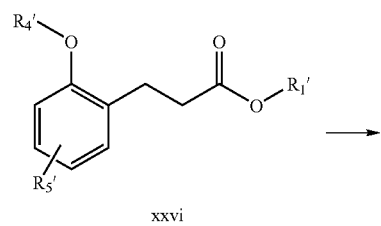

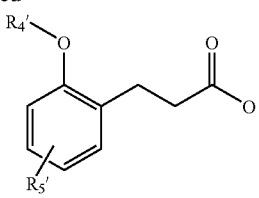

xxvii

As shown in Scheme 7, a solution of substituted salicylic acid xx, where $R_5'$ is H, halogen, lower alkyl, or alkoxy, in a solvent such as DMF can be reacted with a base, typically potassium carbonate, and an alkyl halide with heating to give xxi. This ester can be hydrolyzed by heating with a strong base, typically lithium hydroxide in an aqueous/organic mixed solvent, typically THF, to give the substituted-benzoic acid xxii, where $R_4'$ is lower alkyl or cycloalkyl and $R_5'$ is H, halogen, lower alkyl, or alkoxy.

A solution of substituted-benzoic acid xxii and N,O-dimethylhydroxylamine hydrochloride in an appropriate solvent, typically DMF, with a base, typically triethylamine, can be reacted with a suitable coupling reagent, typically HBTU, to form the "Weinreb" amide xxiii.

Amide xxiii can be reduced with lithium aluminum hydride in THF to afford aldehyde xxiv. Without purification, aldehyde xiv can be treated with a solution of triethylphosphonoacetate and sodium hydride in an appropriate solvent, typically THF, to yield acrylate ester xxv, where $R_1'$ is lower alkyl, $R_4'$ is lower alkyl or cycloalkyl and $R_5'$ is H, halogen, lower alkyl, or alkoxy.

Phenyl-acrylate ester xxv can be hydrogenated in an appropriate solvent with a catalyst, typically 10% palladium on carbon, under an atmosphere of hydrogen, typically 50 psi, to give substituted phenyl-propionate ester xxvi, where $R_1'$ is lower alkyl. Phenyl-propionate ester xxvi can be hydrolyzed by heating with a strong base, typically lithium hydroxide in an aqueous/organic mixed solvent, typically THF, to give the o-substituted-phenyl-propionic acid xxvii where $R_4'$ is lower alkyl or cycloalkyl and $R_5'$ is H, halogen, lower alkyl, or alkoxy.

Scheme 8

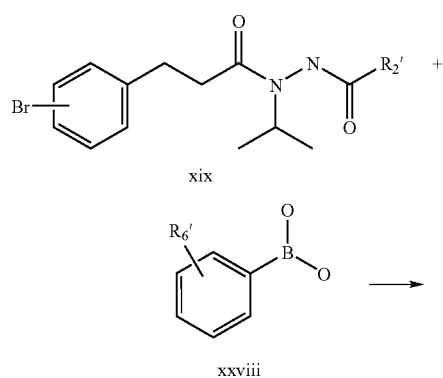

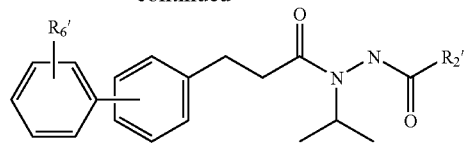

xxix

As shown in Scheme 8, using standard palladium catalyzed "cross coupling" procedures, xix can be heated with a substituted arylboronic acid xxviii in the presence of a base, typically an aqueous solution of sodium carbonate in an appropriate solvent, typically, DME, DMF or toluene, with a catalytic amount of palladium, typically Pd[PPh$_3$]$_4$, to yield xxix, where $R_6'$ is H, halogen, lower alkyl, nitro, alkoxy, thioalkoxy, haloalkoxy, lower alkyl carboxylate, alkyl sulfonyl, or substituted aryl.

Scheme 9

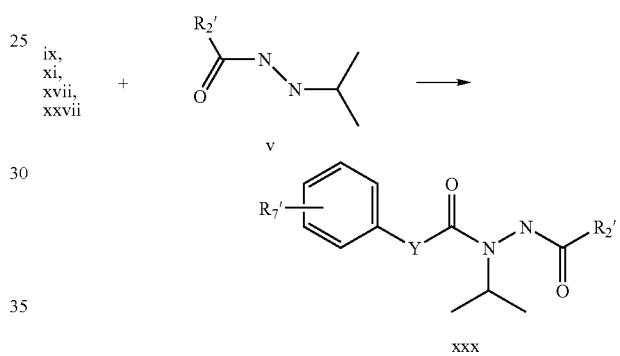

xxx

As shown in Scheme 9, a substituted aryl-acrylic or aryl-propionic acid ix, xi, xvii, or xxvii from Schemes 3, 4, 5, or 7, can be used to acylate a hydrazide v from Scheme 2, where $R_2'$ is aryl, substituted aryl, heteroaryl, substituted heteroaryl, cycloalkyl or cycloheteroalkyl. Various standard amide bond forming conditions, as practiced by those skilled in the art, may be used. Typically, ix, xi, xvii, or xxvii and hydrazide v, in an appropriate solvent, may be treated with a base, such as triethyl amine, and PyBroP or EDCI and HOBT to yield acyl hydrazide xxx, where $R_7'$ is aryl, substituted aryl, heteroaryl, substituted heteroaryl, cycloalkyl or cycloheteroalkyl and Y is ethyl or ethylene.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 10 to about 1000 mg per day.

The invention will now be further described in the Examples below, which are intended as an illustration only and do not limit the scope of the invention.

EXAMPLES

General Methods: Melting points were taken on a Thomas-Hoover apparatus and are uncorrected. Optical rotations were determined with a Perkin-Elmer model 241 polarimeter. 1H-NMR spectra were recorded with Varian XL-200, Mercury-300 or Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230-400 mesh silica gel for flash chromatography; columns were run under a 0-5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to I2 vapor, or by spraying with either phosphomolybdic acid (PMA) in aqueous ethanol, or after exposure to $Cl_2$, with a 4,4'-tetramethyl-diaminodiphenylmethane reagent prepared according to E. Von Arx, M. Faupel and M Brugger, *J Chromatography*, 1976, 220, 224-228.

Reversed phase high pressure liquid chromatography (RP-HPLC) was carried out using a Rainin HPLC employing a 41.4×300 mm, 8 uM, Dynamax™ C-18 column at a flow of 49 mL/min employing a gradient of acetonitrile:water (each containing 0.75% TFA) typically from 5 to 95% acetonitrile over 35-40 min. HPLC conditions are typically described in the format (5-95-35-214); this refers to a linear gradient of from 5% to 95% acetonitrile in water over 35 min while monitoring the effluent with a UV detector at a wavelength of 214 nM.

Methylene chloride (dichloromethane), 2-propanol, DMF, THF, toluene, hexane, ether, and methanol, were Fisher or Baker reagent grade and were used without additional purification except as noted, acetonitrile was Fisher or Baker HPLC grade and was used as is.

Definitions as used herein:

DGAT is diacylglycerol:acyl CoA O-acyltransferase,

THF is tetrahydrofuran,

DMF is N,N-dimethylformamide,

DMA is N,N-dimethylacetamide,

DMSO is dimethylsulfoxide,

DCM is dichloromethane,

DME is dimethoxyethane,

MeOH is methanol,

EtOH is ethanol, $Pd[PPh_3]_4$ is tetrakis(triphenylphosphine)palladium (0),

NaOH is sodium hydroxide,

TFA is 1,1,1-trifluoroacetatic acid,

HOBT is 1-hydroxybenzotriazole,

HBTU is O-benzotriazol-1-yl-N,N,N',N'-tetramethyluronium hexafluorophosphate,

PyBroP is bromotripyrrolidinophosphonium hexafluorophosphate,

EDCI is 1-[3-(dimethylamino)propyl]-3-ethylcarbodiimide hydrochloride,

DIPEA is diisopropylethylamine, brine is saturated aqueous sodium chloride solution, DAG is 1,2-dioleoyl-sn-glycerol, TLC is thin layer chromatography, RP HPLC is reversed phase high performance liquid chromatography, APCI-MS is atmospheric pressure chemical ionization mass spectrometry, ES-MS is electrospray mass spectrometry, RT is room or ambient temperature.

Silica gel chromatography on Biotage columns refers to use of a flash chromatography system supplied by the Biotage Division of the Dyax Corporation employing prepacked 40 g (40 s columns), 90 g (40 m columns) or 800 g (75 m columns). Elution is carried out with hexane-ethyl acetate mixtures under 10-15 psi nitrogen pressure.

Part I: Preparation of Preferred Intermediates

Benzoic acid N'-isopropyl-hydrazide

Furan-2-carboxylic acid N'-isopropyl-hydrazide

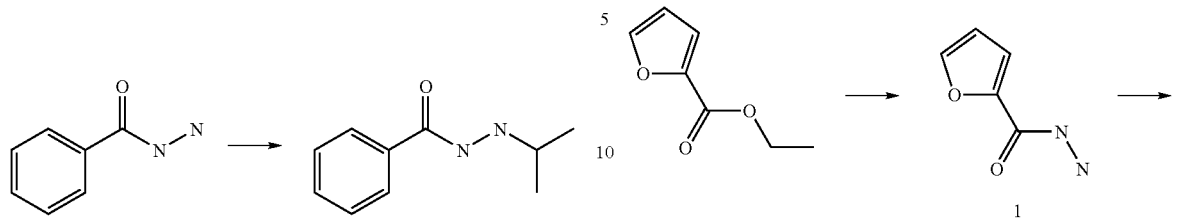

A solution of benzoylhydrazine (10 g, 73.45 mmol) in hexane (200 ml) was treated with acetone (54 mL, 734.5 mmol) and refluxed overnight. The precipitate was collected by suction filtration to afford a white solid which was treated with TFA (200 ml) and triethylsilane (24 mL, 149.24 mmol) at 60° C. overnight. The reaction mixture was concentrated under reduced pressure. The residue was partitioned between DCM and 1N NaOH. The organic layer was washed with brine, dried over sodium sulfate, filtered, and concentrated to afford the product as a white solid (9.31 g, 71%).

A solution of ethyl-2-furoate (2 g, 14.3 mmol) and hydrazine monohydrate (6.9 ml, 143 mmol) in EtOH (10 ml) was refluxed overnight. The mixture was concentrated to dryness to afford intermediate 1 (1.65 g). A portion of this material (500 mg) was dissolved in acetone (5 ml) and the solution was heated to 50° C. overnight. The solution was concentrated to dryness. The residue was dissolved in TFA (5 ml) and treated with triethylsilane (1.30 ml, 8.18 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a white solid (511 mg, 74%).

Thiophene-2-carboxylic acid N'-isopropyl-hydrazide

Thiophene-3-carboxylic acid N'-isopropyl-hydrazide

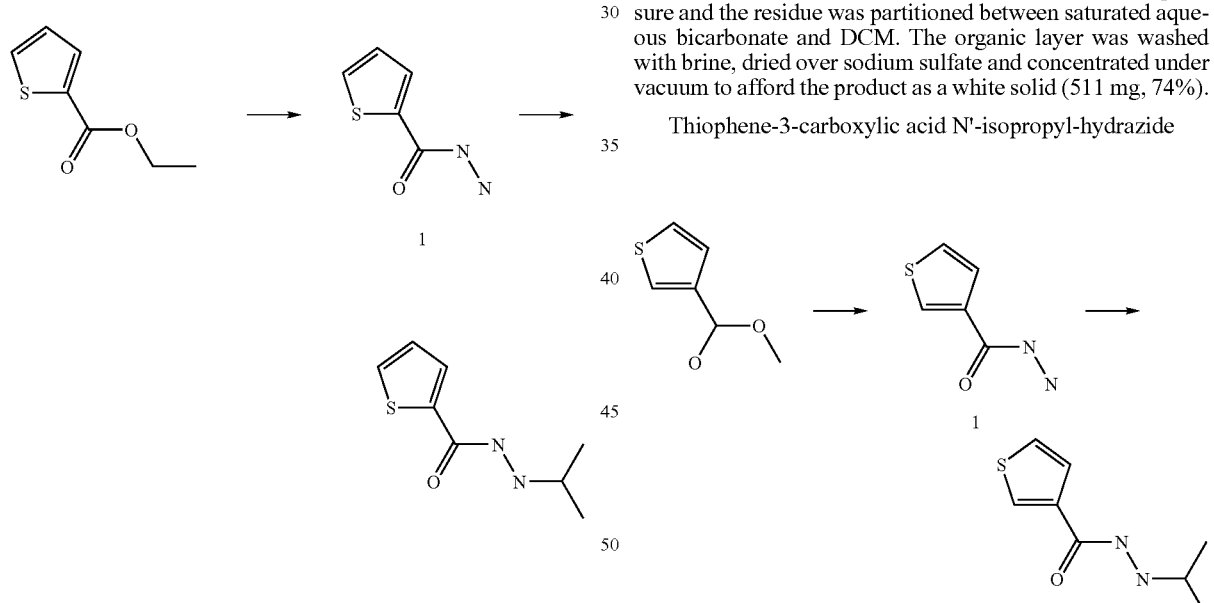

A solution of ethyl-2-thiophene carboxylate (2 g, 12.8 mmol) and hydrazine monohydrate (6.2 ml, 128 mmol) in EtOH (10 ml) was refluxed overnight. The mixture was concentrated to dryness to afford intermediate 1 as an off white solid (1.81 g). A portion of this material (500 mg) was dissolved in acetone (5 ml) and the solution was heated to 50° C. overnight. The solution was concentrated to dryness. The residue was dissolved in TFA (5 ml) and treated with triethylsilane (1.1 ml, 6.74 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a white solid (516 mg, 80%).

A solution of ethyl-3-thiophene carboxylate (2 g, 12.8 mmol) and hydrazine monohydrate (6.2 ml, 128 mmol) in EtOH (10 ml) was refluxed overnight. The mixture was concentrated to dryness to afford intermediate 1 (1.86 g, 100%). A portion of this material (500 mg) was dissolved in acetone (5 ml) and the solution was heated to 60° C. overnight. The solution was concentrated to dryness. The residue was dissolved in TFA (5 ml) and treated with triethylsilane (1.16 ml, 7.24 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a white solid (484 mg, 75%).

4-(2-Methoxy-ethoxy)-benzoic acid-N'-isopropyl hydrazide

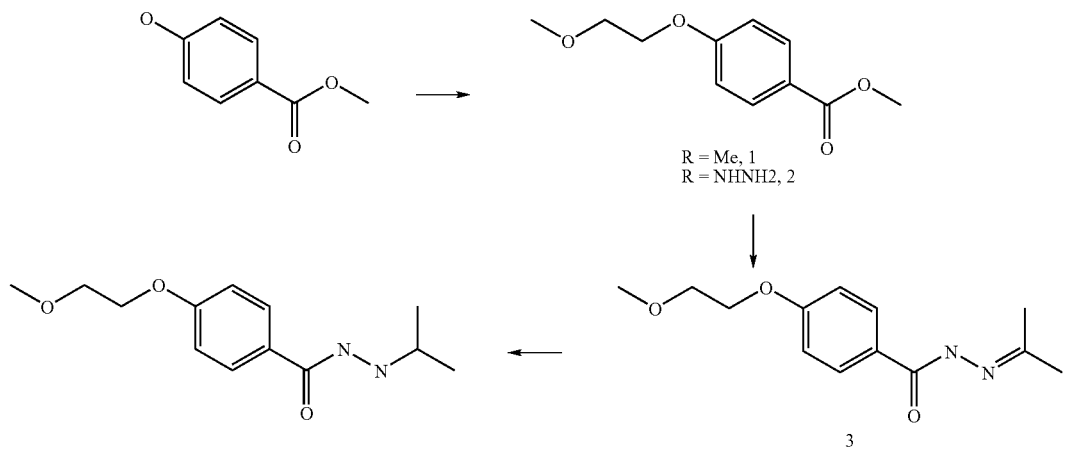

A DMF (20 ml) solution of methyl-p-hydroxybenzoate (1.0 g, 6.57 mmol), potassium carbonate (9.08 g, 65.72 mmol) and 2-bromoethyl methyl ether (6.17 ml, 65.72 mmol) was heated to 150° C. for 20 minutes in a microwave oven. The reaction mixture was filtered through celite, and partitioned between 1 N NaOH and ethyl acetate. The organic layer was washed with brine, dried over sodium sulfate, filtered and concentrated to afford intermediate 1 as pale yellow oil (1.28 g, 93%). A solution of ester 1 (1.0 g, 4.76 mmol) and hydrazine monohydrate (4.61 ml, 95.12 mmol) in MeOH (8 ml) was heated to 160° C. for 20 minutes in a microwave oven. The reaction mixture was concentrated under reduced pressure to afford hydrazide 2 as a yellow solid (790 mg, 79%). A solution of hydrazide 2 (200 mg, 0.95 mmol) in acetone (4 ml) was refluxed overnight. The reaction mixture was concentrated under reduced pressure to afford intermediate 3 as brown oil (240 mg, 100%). Compound 3 (240 mg, 0.95 mmol) was then treated with EtSiH (0.35 ml, 2.1 mmol) in TFA (5 ml) at 60° C. overnight. The reaction mixture was concentrated and the residue was partitioned between DCM and 1N NaOH. The organic layer was washed with brine, dried over sodium sulfate, filtered and concentrated to afford the product as oil (170 mg, 62%).

2-(2-Methoxy-ethoxy)-benzoic acid-N'-isopropyl hydrazide

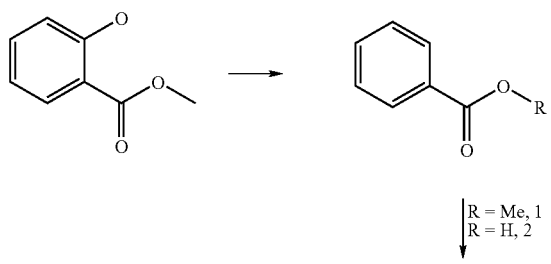

-continued

A DMF (20 ml) solution of methyl-o-hydroxybenzoate (1.0 g, 6.57 mmol), potassium carbonate (9.08 g, 65.72 mmol) and 2-bromoethyl methyl ether (6.17 ml, 65.72 mmol) was heated to 150° C. for 20 minutes in a microwave oven. The reaction mixture was filtered through celite, and partitioned between 1 N NaOH and ethyl acetate. The organic layer was washed with brine, dried over sodium sulfate, filtered and concentrated to afford intermediate 1 as brown oil (807 mg, 58%). A solution of ester 1 (0.8 g, 3.8 mmol) and hydrazine monohydrate (4.0 ml, 76.0 mmol) in MeOH (8 ml) was heated to 160° C. for 20 minutes in a microwave oven. The reaction mixture was concentrated under reduced pressure to afford hydrazide 2 as oil (840 mg, 88%). A solution of hydrazide 2 (840 mg, 3.99 mmol) in acetone (10 ml) was refluxed overnight. The reaction mixture was concentrated under reduced pressure to afford intermediate 3 as brown oil (1.1 g, 100%). This crude material was then treated with EtSiH (1.5 ml, 9.25mmol) in TFA (25 ml) at 60° C. overnight. The reaction mixture was concentrated and the residue was partitioned between DCM and 1N NaOH. The organic layer was washed with brine, dried over sodium sulfate, filtered and concentrated to afford the product as oil (460 mg, 40%).

3-(2',3'-Dimethyl-biphenyl-2-yl)-acrylic acid ethyl ester

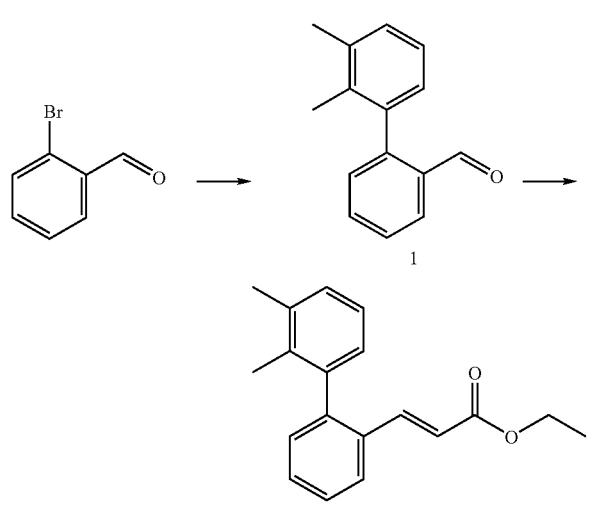

A solution of 2-bromo-benzaldehyde (150 mg, 0.81 mmol) in DME (2 ml)/2M Na$_2$CO$_3$ (1.4 ml, 2.84 mmoles) was treated with 3-dimethyl-phenylboronic acid (243 mg, 1.62 mmol) and Pd[PPh$_3$]$_4$ (93 mg, 0.081 mmol) for 10 min at 150° C. in a microwave reactor. The reaction mixture was partitioned between water and ethyl acetate. The organic layer was washed successively with water and brine, then dried over sodium sulfate, filtered, and concentrated. The crude was absorbed on silica and purified on a silica gel column with a 1-5% ethyl acetate/hexanes gradient to afford 1 (746 mg, 87%).

A solution of triethylphosphonoacetate (0.226 ml, 1.14 mmoles) in THF (10 ml) was treated with 60% sodium hydride (87 mg, 2.18 mmoles) at rt for 10 min. The aldehyde 1 (200 mg, 0.95 mmoles) was then added and the solution was stirred at rt for 2.5 h. The reaction mixture was partitioned between 1 N HCl and ethyl acetate. The organic layer was washed successively with water, saturated sodium carbonate and brine, then dried over sodium sulfate, filtered and concentrated. The crude was absorbed on silica and purified on a silica gel column with a 5-10% ethyl acetate/hexanes gradient to afford 3-(2',3'-dimethyl-biphenyl)-acrylic acid ethyl ester (234 mg, 88%).

3-(2',3'-Dimethyl-biphenyl-2-yl)-acrylic acid

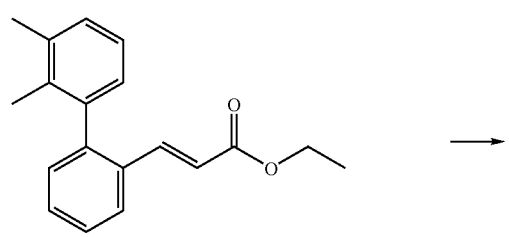

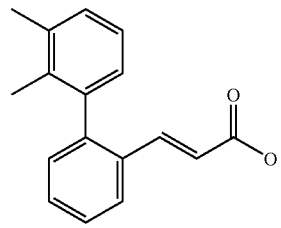

A solution of 3-(2',3'-dimethyl-biphenyl-2-yl)-acrylic acid ethyl ester (110 mg, 0.39 mmoles) in THF (3 ml)/2N NaOH (3 ml) was heated to 160° C. for 10 min in a microwave reactor. The mixture was cooled to rt and partitioned between 1N HCl and ethyl acetate. The organic layer was washed with water and brine, then dried over sodium sulfate and concentrated to afford the desired acid (100 mg, 100%).

3-(2',3'-Dimethyl-biphenyl-2-yl)-propionic acid

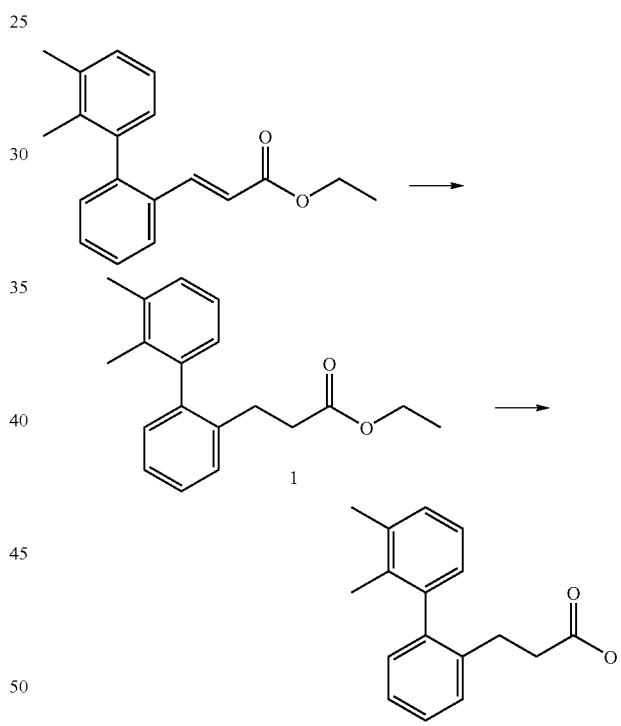

A solution of 3-(2',3'-dimethyl-biphenyl-2-yl)-acrylic acid ethyl ester (2.3 g, 8.2 mmoles) in MeOH (35 ml) was placed in the Parr apparatus. A catalytic amount of 10% Pd/C (230 mg) was added and the mixture was shaken under an atmosphere of hydrogen (50 psi) for 1.5 h. The heterogeneous mixture was filtered through a cake of celite and concentrated to afford ester 1 (2.17 g). This intermediate was dissolved in THF (40 ml)/water (20 ml) and treated with lithium hydroxide monohydrate (3.23 g, 76.8 mmoles) for 5 h at reflux. The mixture was cooled to rt and partitioned between 1N HCl and ethyl acetate. The organic layer was washed with water and brine, then dried over sodium sulfate and concentrated to afford the desired acid (1.94 g, 93%).

3-(2-Phenoxy-phenyl)-propionic acid

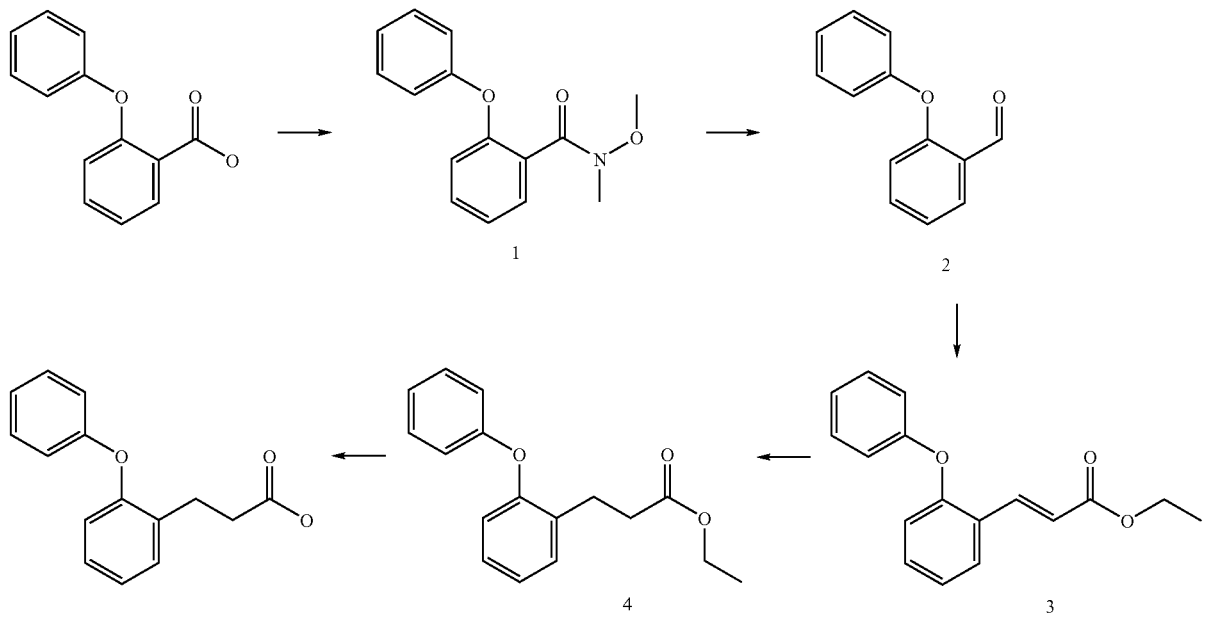

A solution of 2-phenoxybenzoic acid (660 mg, 3.08 mmoles) and N,O-dimethylhydroxylamine hydrochloride (451 mg, 4.62 mmoles) in DMF (15 ml) was treated at rt for 18 h with triethylamine (1.3 ml, 9.24 mmoles) and HBTU (1.75 g, 4.62 mmoles). The reaction mixture was partitioned between 1N NaOH and ethyl acetate. The organic layer was washed with brine, dried over sodium sulfate and concentrated to afford 1 which was not further purified (827 mg, 100%).

A 1M solution of lithium aluminum hydride in THF (3.18 ml, 3.18 mmoles) was slowly added to a cold (−20° C.) solution of 1 (410 mg, 1.59 mmoles) in THF (8 ml). The solution was stirred at −20° C. for 45 min and then quenched slowly with water. The mixture was filtered through a cake of celite and the filtrate was partitioned between ethyl acetate and saturated bicarbonate. The organic layer was washed with brine, dried over sodium sulfate and concentrated to afford aldehyde 2 (278 mg, 88%) which was not further purified.

A solution of triethylphosphonoacetate (0.334 ml, 1.68 mmoles) in THF (2 ml) was treated with 60% sodium hydride (132 mg, 3.3 mmoles) at rt for 10 min. The aldehyde 2 (278 mg, 1.40 mmoles) was then added and the solution was stirred at rt for 4 h. The reaction mixture was partitioned between 1 N HCl and ethyl acetate. The organic layer was washed successively with water, saturated sodium carbonate and brine, then dried over sodium sulfate, filtered and concentrated. The crude was adsorbed on silica and purified on a silica gel column with a 5-10% ethyl acetate/hexanes gradient to afford ester 3 (258 mg, 59%).

A solution of ester 3 (136 mg, 0.51 mmoles) in EtOH (5 ml) was placed in the Parr apparatus. A catalytic amount of 10% Pd/C (25 mg) was added and the mixture was shaken under an atmosphere of hydrogen (50 psi) for 1.5 h. The heterogeneous mixture was filtered through a cake of celite and concentrated to afford ester 4 (127 mg, 93%).

This ester (127 mg, 0.47 mmoles) was dissolved in THF (10 ml)/ water (5 ml) and treated with lithium hydroxide monohydrate (197 mg, 4.7 mmoles) for 5 h at reflux. The mixture was cooled to rt and partitioned between 1N HCl and ethyl acetate. The organic layer was washed with water and brine then dried over sodium sulfate and concentrated to afford the desired acid (112 mg, 98%).

Benzoic acid N'-[3-(2-bromo-phenyl)-propionyl]-N'-isopropyl-hydrazide

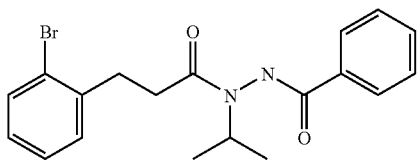

A solution of (3-(2-bromophenyl)propionic acid (257 mg, 1.12 mmoles) and benzoic acid N'-isopropyl-hydrazide (200 mg, 1.12 mmoles) in DMF (6 mL) was treated with triethylamine (0.47 mL, 3.36 mmol), HOBT (182 mg, 1.34 mmoles) and EDCI (2.58 g, 1.34 mmol) at room temperature for 72 h. The reaction mixture was partitioned between water and dichloromethane. The organic layer was successively washed with water and brine, then dried over sodium sulfate, filtered and concentrated. The crude was absorbed on silica and purified on a silica gel column with a 20-30% ethyl acetate/hexanes gradient to afford the product as a solid (258 mg, 59%).

Benzoic acid N'-[3-(4-bromo-phenyl)-propionyl]-N'-isopropyl-hydrazide

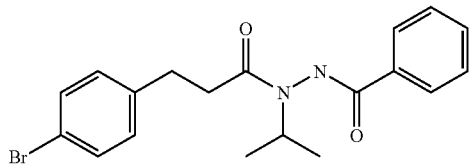

A solution of (3-(4-bromophenyl)propionic acid (387 mg, 1.68 mmoles) and benzoic acid N'-isopropyl-hydrazide (300 mg, 1.68 mmoles) in DMF (10 mL) was treated with triethylamine (0.70 mL, 5.05 mmol), HOBT (273 mg, 2.02 mmoles) and EDCI (387 mg, 2.02 mmoles) at room temperature for 72 h. The reaction mixture was partitioned between 1N HCl and ethyl acetate. The organic layer was successively washed with water, 1N NaOH and brine, then dried over sodium sulfate, filtered and concentrated to afford the product as a solid (476 mg, 73%). The product was not further purified.

General Procedure for 3-(2-alkoxy-3-fluoro-phenyl)-propionic acids

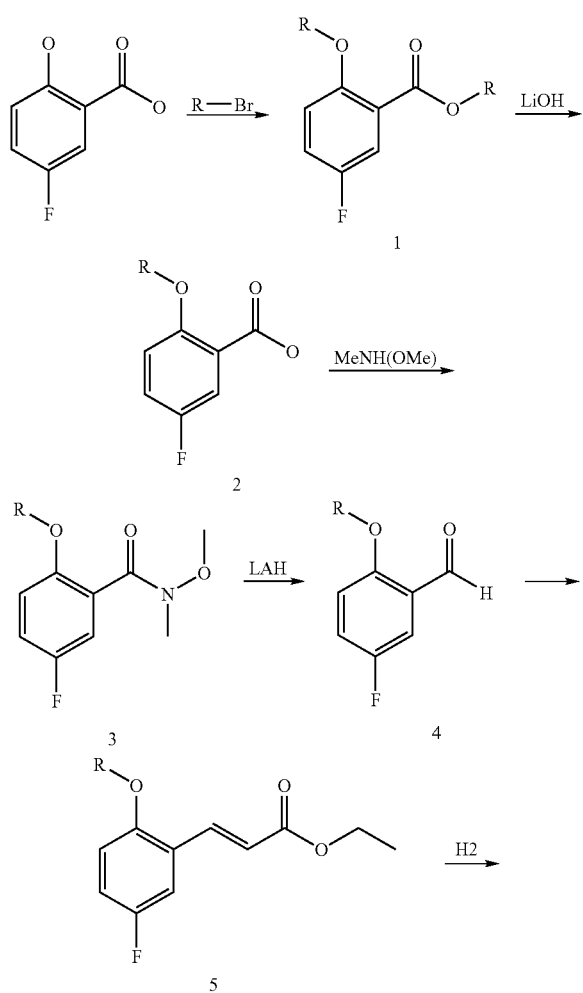

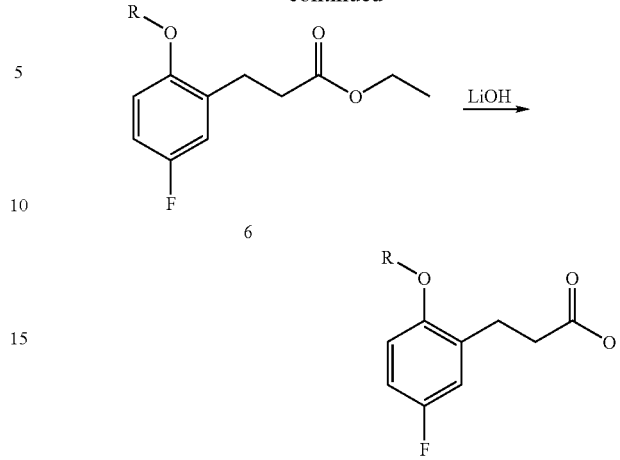

A solution of 5-fluoro-salicylic acid in DMF (0.2M) was reacted with potassium carbonate (5 eq) and an alkyl bromide (4 eq) at 80° C. for 2-3 h. The reaction mixture was partitioned between 1N HCl and ethyl acetate. The organic layer was washed successively with 1N NaOH and brine, then dried over sodium sulfate, filtered, and concentrated to afford intermediate 1 which was not further purified.

This compound was dissolved in THF (0.2M) and treated with lithium hydroxide monohydrate (10 eq) at reflux overnight. The reaction mixture was partitioned between 1N HCl and ethyl acetate. The organic layer was washed with brine, dried over sodium sulfate, filtered, and concentrated to afford acid 2 which was not further purified.

A solution of 2 in DMF (0.2M) was treated with triethylamine (5 eq), N,O-dimethylamine hydrochloride (1.5 eq) and HBTU (1.5 eq) at rt overnight. The reaction mixture was partitioned between 1N HCl and ethyl acetate. The organic layer was washed with brine, dried over sodium sulfate, filtered, and concentrated to afford amide 3 which was not further purified.

A solution of 3 in anhydrous THF (0.2M) was cooled to −30° C. and then treated with a THF solution of lithium aluminum hydride (1M, 2 eq) for 10 min. The reaction was quenched at −30° C. with 1N HCl and extracted with ethyl acetate. The organic layer was washed with brine, dried over sodium sulfate, filtered, and concentrated to afford aldehyde 4 which was not further purified.

A THF solution of triethylphosphonoacetate (0.2M) was treated at rt for 10 min with 60% sodium hydride (2 eq). A THF solution of 4 (0.2M, 1 eq) was then added at rt and the mixture was stirred for 2-3h. The reaction was quenched at rt with 1N HCl and extracted with ethyl acetate. The organic layer was washed successively with saturated aqueous sodium bicarbonate and brine, then dried over sodium sulfate, filtered, and concentrated. The crude was absorbed on silica and purified on a silica gel column with 5% ethyl acetate/hexanes to afford ester 5.

A solution of 5 in ethanol (0.2M) was placed in the Parr apparatus. A catalytic amount of 10% Pd/C (50 mg/mmol) was added and the mixture was shaken under an atmosphere of hydrogen (50 psi) for 2-3h. The heterogeneous mixture was filtered through a cake of celite and concentrated to afford ester 6 which was not further purified.

This compound was dissolved in THF/H$_2$O (2/1) (0.2M) and treated with lithium hydroxide monohydrate (10 eq) at reflux for 4-5 h. The reaction mixture was partitioned between 1N HCl and ethyl acetate. The organic layer was washed with brine, dried over sodium sulfate, filtered, and concentrated to afford the corresponding phenyl propionic acid which was not further purified.

Phenyl propionic acids were prepared by this method where R=n-propyl, n-butyl, cyclopentyl, and cyclobutylmethyl.

Part II: Preparation of Preferred Compounds

Example 1

Benzoic acid N'-[3-biphenyl-2-yl-propionyl]-N'-isopropyl-hydrazide

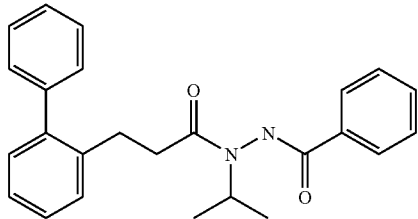

A solution of benzoic acid N'-[3-(2-bromo-phenyl)-propionyl]-N'-isopropyl-hydrazide (100 mg, 0.26 mmol) in DME (5 ml)/2M Na$_2$CO$_3$ (450 μL, 0.90 mmol) was treated with phenylboronic acid (47 mg, 0.39 mmol) and Pd[PPh$_3$]$_4$ (30 mg, 0.026 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 30-50% ethyl acetate/hexanes gradient to afford the product as a solid (98 mg, 98%). LC-MS m/e 387.16 (M+H$^+$)

Example 2

Benzoic acid N'-isopropyl-N'-[3-(3'-trifluoromethyl-biphenyl-2-yl)-propionyl]-hydrazide

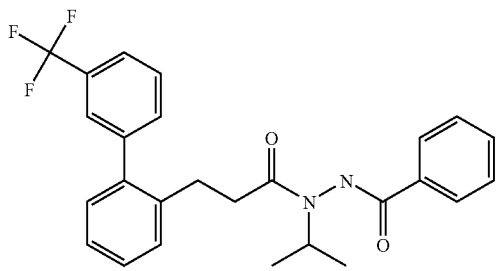

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 3-trifluoro-phenylboronic acid (49 mg, 0.26 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient and then by RP HPLC to afford the product as a solid (15 mg, 26%). LC-MS m/e 455.21 (M+H$^+$)

Example 3

Benzoic acid N'-[3-(3'-ethoxy-biphenyl-2-yl)-propionyl]-N'-isopropyl-hydrazide

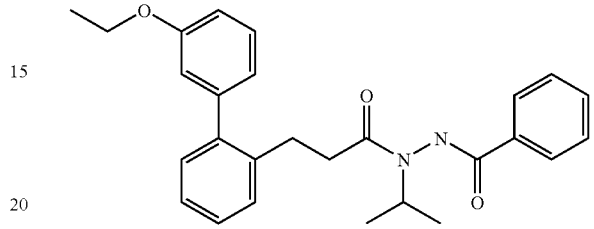

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 3-ethoxy-phenylboronic acid (42 mg, 0.26 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient and then by RP HPLC to afford the product as a solid (12 mg, 22%). LC-MS m/e 431.27 (M+H$^+$)

Example 4

Benzoic acid N'-[3-(3'-cyano-biphenyl-2-yl)-propionyl]-N'-isopropyl-hydrazide

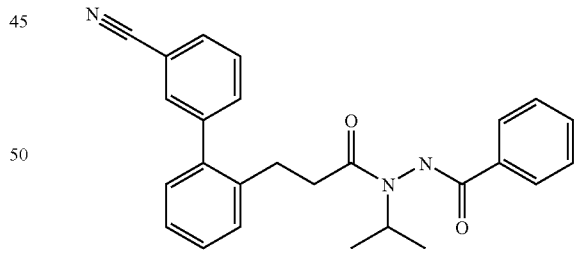

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 3-cyano-phenylboronic acid (38 mg, 0.26 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (13 mg, 25%). LC-MS m/e 412.21 (M+H$^+$)

Example 5

Benzoic acid N'-[3-(5'-chloro-2'-methoxy-biphenyl-2-yl)-propionyl]-N'-isopropyl-hydrazide

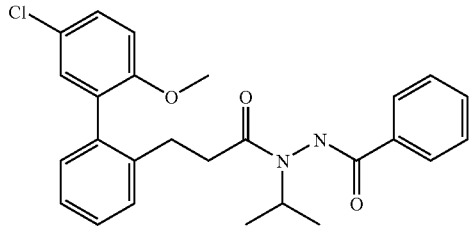

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 5-chloro-2-methoxy-phenylboronic acid (48 mg, 0.26 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (22 mg, 38%). LC-MS m/e 451.31 (M+H$^+$)

Example 6

Benzoic acid N'-isopropyl-N'-[3-(3'-nitro-biphenyl-2-yl)-propionyl]-hydrazide

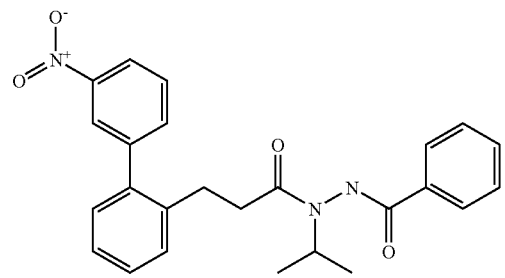

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 3-nitro-phenylboronic acid (43 mg, 0.26 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (12 mg, 22%). LC-MS m/e 432.31 (M+H$^+$)

Example 7

Benzoic acid N'-[3-(3'-chloro-4'-fluoro-biphenyl-2-yl)-propionyl]-N'-isopropyl-hydrazide

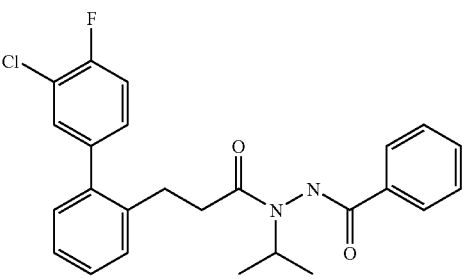

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 3-chloro-4-fluoro-phenylboronic acid (34 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient and then by RP HPLC to afford the product as a solid (23 mg, 41%). LC-MS m/e 439.25 (M+H$^+$)

Example 8

Benzoic acid N'-[3-(5'-isopropyl-2'-methoxy-biphenyl-2-yl)-propionyl]-N'-isopropyl-hydrazide

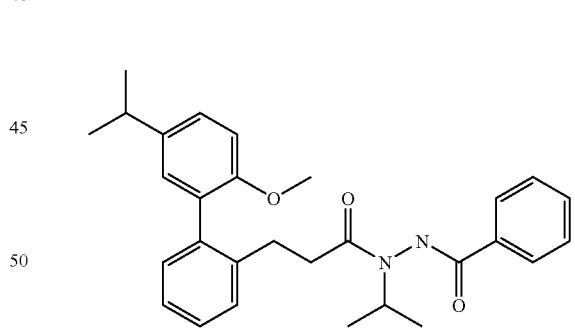

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 5-isopropyl-2-methoxy-phenylboronic acid (37 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient and then by RP HPLC to afford the product as a solid (18 mg, 31%). LC-MS m/e 459.35 (M+H$^+$)

Example 9

Benzoic acid N'-[3-(2',5'-dimethyl-biphenyl-2-yl)-propionyl]-N'-isopropyl-hydrazide

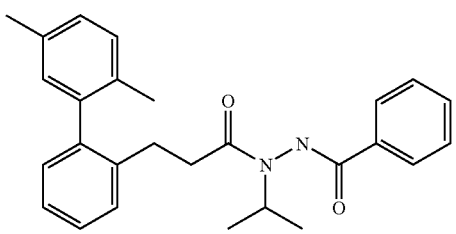

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 2,5-dimethyl-phenylboronic acid (29 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (14 mg, 26%). LC-MS m/e 415.36 (M+H$^+$)

Example 10

Benzoic acid N'-[3-(5'-fluoro-2'-methoxy-biphenyl-2-yl)-propionyl]-N'-isopropyl-hydrazide

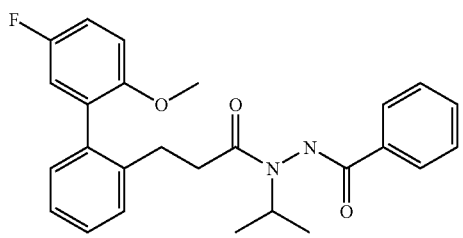

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 5-fluoro-2-methoxy-phenylboronic acid (33 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (18 mg, 32%). LC-MS m/e 435.33 (M+H$^+$)

Example 11

Benzoic acid N'-[3-(3'-isopropyl-biphenyl-2-yl)-propionyl]-N'-isopropyl-hydrazide

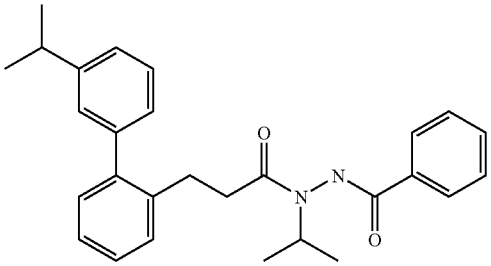

A solution of benzoic acid N'-[3-(2-bromo-phenyl)-propionyl]-N'-isopropyl-hydrazide (50 mg, 0.13 mmol) in DME (4 ml) 2M Na$_2$CO$_3$ (225 μL, 0.45 mmol) was treated with 3-isopropyl-phenylboronic acid (32 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (17 mg, 31%). LC-MS m/e 429.39 (M+H$^+$)

Example 12

Benzoic acid N'-[3-(4'-fluoro-2'-methyl-biphenyl-2-yl)-propionyl]-N'-isopropyl-hydrazide

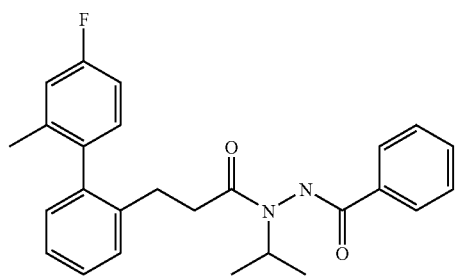

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 μL, 0.45 mmol) was treated with 4-fluoro-2-methyl-phenylboronic acid (30 mg, 0.19 mmol) and Pd[PPh$_3$]$_4$ (15 mg, 0.013 mmol) for 72 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient and then by RP HPLC to afford the product as a solid (5 mg, 9%). LC-MS m/e 419.28 (M+H$^+$)

Example 13

Benzoic acid N'-isopropyl-N'-[3-(3'-methyl-biphenyl-2-yl)-propionyl]-hydrazide

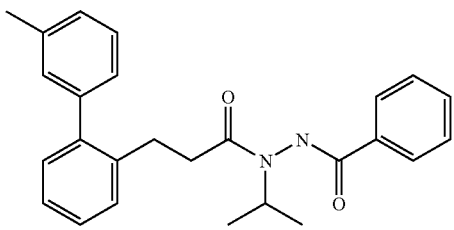

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 µL, 0.45 mmol) was treated with 3-methyl-phenylboronic acid (26 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (48 mg, 93%). LC-MS m/e 401.37 (M+H$^+$)

Example 14

Benzoic acid N'-isopropyl-N'-[3-(3'-methoxy-biphenyl-2-yl)-propionyl]-hydrazide

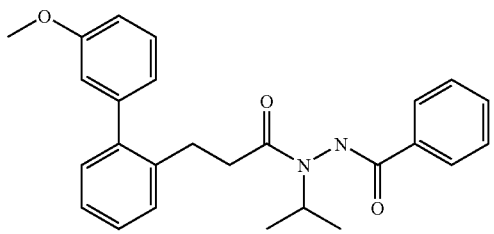

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 µL, 0.45 mmol) was treated with 3-methoxy-phenylboronic acid (29 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (32 mg, 60%). LC-MS m/e 417.35 (M+H$^+$)

Example 15

Benzoic acid N'-[3-(3'-chloro-biphenyl-2-yl)-propionyl]-N'-isopropyl-hydrazide

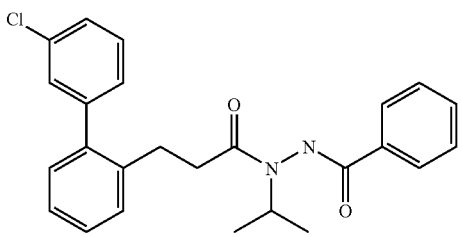

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 µL, 0.45 mmol) was treated with 3-chloro-phenylboronic acid (30 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (39 mg, 72%). LC-MS m/e 421.26 (M+H$^+$)

Example 16

Benzoic acid N'-[3-(3'-fluoro-biphenyl-2-yl)-propionyl]-N'-isopropyl-hydrazide

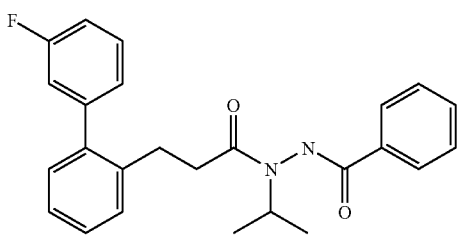

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 µL, 0.45 mmol) was treated with 3-fluoro-phenylboronic acid (27 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (38 mg, 73%). LC-MS m/e 405.28 (M+H$^+$)

Example 17

Benzoic acid N'-[3-(2'-fluoro-biphenyl-2-yl)-propionyl]-N'-isopropyl-hydrazide

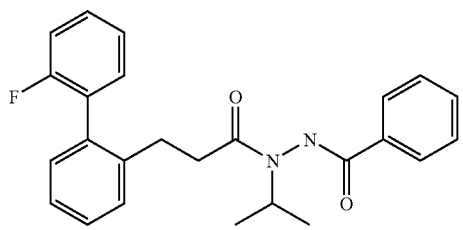

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 µL, 0.45 mmol) was treated with 2-fluoro-phenylboronic acid (27 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (13 mg, 25%). LC-MS m/e 405.28 (M+H$^+$)

Example 18

Benzoic acid N'-isopropyl-N'-[3-(2'-methyl-biphenyl-2-yl)-propionyl]-hydrazide

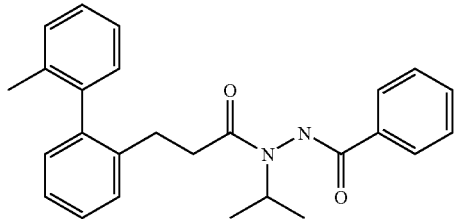

A solution of benzoic acid N'-[3-(2-bromo-phenyl)-propionyl]-N'-isopropyl-hydrazide (50 mg, 0.13 mmol) in DME (4 ml)/2M Na$_2$CO$_3$ (225 µL, 0.45 mmol) was treated with 2-methyl-phenylboronic acid (27 mg, 0.19 mmol) and Pd[PPh$_3$]$_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (9 mg, 18%). LC-MS m/e 401.29 (M+H$^+$)

Example 19

Benzoic acid N'-[3-(2'-chloro-biphenyl-2-yl)-propionyl]-N'-isopropyl-hydrazide

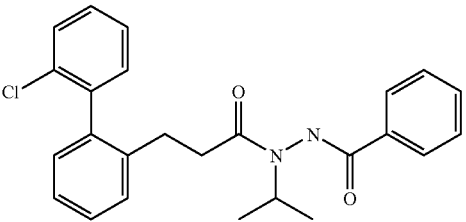

A solution of benzoic acid N'-[3-(2-bromo-phenyl)-propionyl]-N'-isopropyl-hydrazide (45 mg, 0.12 mmol) in DME (4 ml)/2M Na$_2$CO$_3$ (225 µL, 0.45 mmol) was treated with 2-chloro-phenylboronic acid (27 mg, 0.17 mmol) and Pd[PPh$_3$]$_4$ (13 mg, 0.012 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 30-50% ethyl acetate/hexanes gradient to afford the product as a solid (46 mg, 94%). LC-MS m/e 421.27 (M+H$^+$)

Example 20

Benzoic acid N'-[3-(4'-chloro-biphenyl-2-yl)-propionyl]-N'-isopropyl-hydrazide

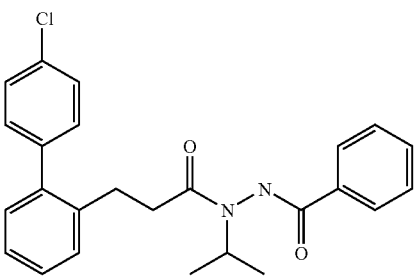

A solution of benzoic acid N'-[3-(2-bromo-phenyl)-propionyl]-N'-isopropyl-hydrazide (45 mg, 0.12 mmol) in DME (4 ml)/2M Na$_2$CO$_3$ (225 µL, 0.45 mmol) was treated with 4-chloro-phenylboronic acid (27 mg, 0.17 mmol) and Pd[PPh$_3$]$_4$ (13 mg, 0.012 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 30-50% ethyl acetate/hexanes gradient to afford the product as a solid (30 mg, 61%). LC-MS m/e 421.26 (M+H$^+$)

Example 21

Benzoic acid N'-isopropyl-N'-[3-(2'-methoxy-biphenyl-2-yl)-propionyl]-hydrazide

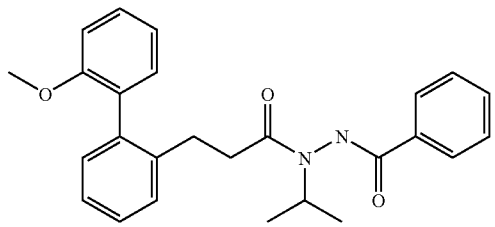

A solution of benzoic acid N'-[3-(2-bromo-phenyl)-propionyl]-N'-isopropyl-hydrazide (50 mg, 0.13 mmol) in DME (4 ml)/2M $Na_2CO_3$ (225 µL, 0.45 mmol) was treated with 2-methoxy-phenylboronic acid (29 mg, 0.19 mmol) and $Pd[PPh_3]_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (21 mg, 39%). LC-MS m/e 417.30 (M+H$^+$)

Example 22

Benzoic acid N'-isopropyl-N'-[3-(4'-methoxy-biphenyl-2-yl)-propionyl]-hydrazide

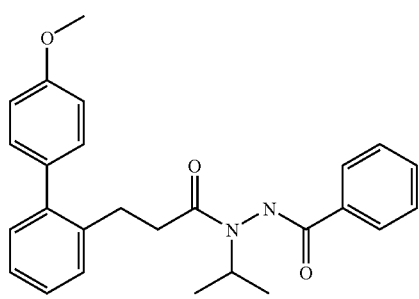

A solution of benzoic acid N'-[3-(2-bromo-phenyl)-propionyl]-N'-isopropyl-hydrazide (50 mg, 0.13 mmol) in DME (4 ml)/2M $Na_2CO_3$ (225 µL, 0.45 mmol) was treated with 4-methoxy-phenylboronic acid (29 mg, 0.19 mmol) and $Pd[PPh_3]_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (35 mg, 66%). LC-MS m/e 417.29 (M+H$^+$)

Example 23

Benzoic acid N'-[3-(4'-fluoro-biphenyl-2-yl)-propionyl]-N'-isopropyl--hydrazide

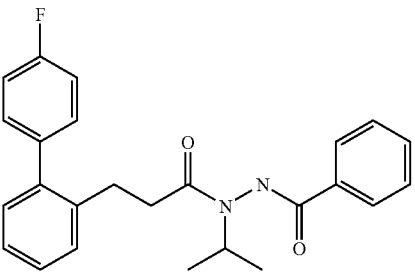

A solution of benzoic acid N'-[3-(2-bromo-phenyl)-propionyl]-N'-isopropyl-hydrazide (50 mg, 0.13 mmol) in DME (4 ml)/2M $Na_2CO_3$ (225 µL, 0.45 mmol) was treated with 4-fluoro-phenylboronic acid (29 mg, 0.19 mmol) and $Pd[PPh_3]_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient to afford the product as a solid (41 mg, 79%). LC-MS m/e 405.25 (M+H$^+$)

Example 24

Benzoic acid N'-[3-(2',3'-dimethyl-biphenyl-2-yl)-propionyl]-N'-isopropyl-hydrazide

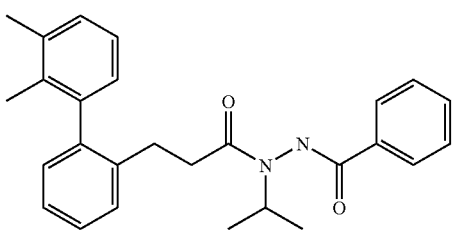

A solution of benzoic acid N'-[3-(2-bromo-phenyl)-propionyl]-N'-isopropyl-hydrazide (50 mg, 0.13 mmol) in DME (4 ml)/2M $Na_2CO_3$ (225 µL, 0.45 mmol) was treated with 2,3-dimethyl-phenylboronic acid (38 mg, 0.26 mmol) and $Pd[PPh_3]_4$ (15 mg, 0.013 mmol) for 18 hours at 90° C. The reaction mixture was partitioned between water and dichloromethane. The organic layer was washed with brine, dried over sodium sulfate, filtered, and concentrated. The crude was absorbed on silica and purified on a silica gel column with a 20-50% ethyl acetate/hexanes gradient and then by RP HPLC to afford the product as a solid (14 mg, 27%). LC-MS m/e 415.35 (M+H$^+$)

Example 25

Benzoic acid N'-[3-biphenyl-3-yl-propionyl]-N'-isopropyl-hydrazide

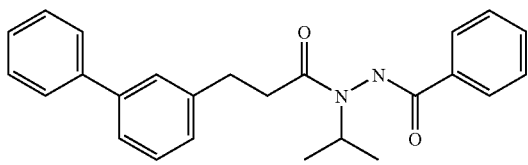

A solution of benzoic acid N'-[3-(3-bromo-phenyl)-propionyl]-N'-isopropyl-hydrazide (100 mg, 0.26 mmol) in DME (5 ml)/2M Na$_2$CO$_3$ (450 μL, 0.90 mmol) was treated with phenylboronic acid (47 mg, 0.39 mmol) and Pd[PPh$_3$]$_4$ (30 mg, 0.026 mmol) for 18 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a solid (69 mg, 70%). LC-MS m/e 387.19 (M+H$^+$)

Example 26

Benzoic acid N'-[3-biphenyl-4-yl-propionyl]-N'-isopropyl-hydrazide

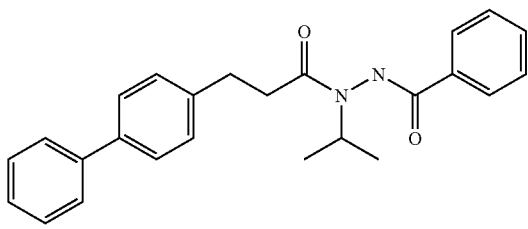

A solution of benzoic acid N'-[3-(4-bromo-phenyl)-propionyl]-N'-isopropyl-hydrazide (100 mg, 0.26 mmol) in DME (5 ml)/2M Na$_2$CO$_3$ (450 μL, 0.90 mmol) was treated with phenylboronic acid (47 mg, 0.39 mmol) and Pd[PPh$_3$]$_4$ (30 mg, 0.026 mmol) for 18 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a solid (56 mg, 56%). LC-MS m/e 387.17 (M+H$^+$)

Example 27

Benzoic acid N'-(2-9H-fluoren-9-yl-acetyl)-N'-isopropyl-hydrazide

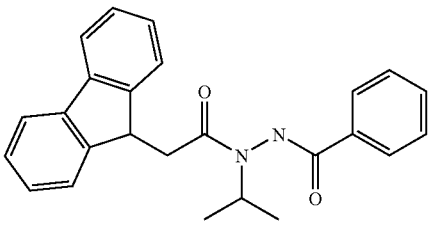

A solution of 9-fluoreneacetic acid (126 mg, 0.56 mmoles) and benzoic acid N'-isopropyl-hydrazide (100 mg, 0.56 mmoles) in DMF (5 mL) was treated with triethylamine (0.23 mL, 1.68 mmol), HOBT (91 mg, 0.67 mmoles) and EDCI (129 mg, 0.67 mmol) at room temperature for 72 h. The reaction mixture was partitioned between water and dichloromethane. The organic layer was washed with water and brine, then dried over sodium sulfate, filtered and concentrated. The crude was absorbed on silica and purified on a silica gel column with a 10-30% ethyl acetate/hexanes gradient to afford the product as a solid (87 mg, 40%). LC-MS m/e 385.19 (M+H$^+$)

Example 28

Benzoic acid N'-(3,3-diphenyl-propionyl)-N'-isopropyl-hydrazide

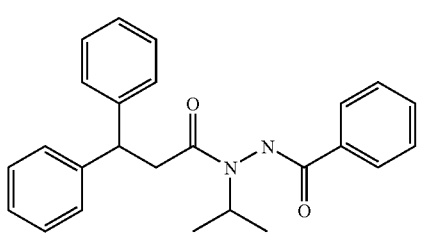

A solution of 3,3-diphenylpropionic acid (127 mg, 0.56 mmoles) and benzoic acid N'-isopropyl-hydrazide (100 mg, 0.56 mmoles) in DMF (5 mL) was treated with triethylamine (0.23 mL, 1.68 mmol), HOBT (91 mg, 0.67 mmoles) and EDCI (129 mg, 0.67 mmol) at room temperature for 18 h. The reaction mixture was partitioned between water and dichloromethane. The organic layer was washed with water, dried over sodium sulfate, filtered and concentrated. The crude was absorbed on silica and purified on a silica gel column with a 30-50% ethyl acetate/hexanes gradient to afford the product as a solid (59 mg, 27%). LC-MS m/e 387.26 (M+H$^+$)

Example 29

Benzoic acid N'-isopropyl-N'-[3-(2-phenoxy-phenyl)-propionyl]-hydrazide

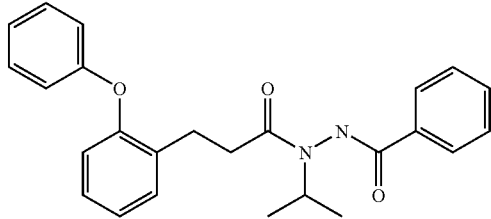

A solution of 3-(2-phenoxy-phenyl)-propionic acid (110 mg, 0.45 mmoles) and benzoic acid N'-isopropyl-hydrazide (97 mg, 0.54 mmoles) in DMF (5 mL) was treated with diisopropylethylamine (0.20 mL, 1.13 mmol), and PyBroP (315 mg, 0.68 mmol) at room temperature for 18 h. The reaction mixture was partitioned between 1N HCl and ethyl acetate. The organic layer was washed with water and brine, dried over sodium sulfate, filtered and concentrated. The crude was absorbed on silica and purified on a silica gel column with a 30-50% ethyl acetate/hexanes gradient to afford the product as a solid (40 mg, 22%). LC-MS m/e 425.44 (M+H$^+$)

Example 30

Benzoic acid N'-[3-(2',3'-dimethyl-biphenyl-2-yl)-acryloyl]-N'-isopropyl-hydrazide

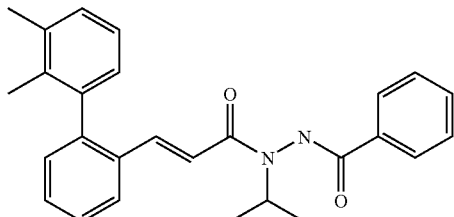

A solution of 3-(2',3'-dimethyl-biphenyl-2-yl)-acrylic acid (120 mg, 0.40 mmoles) and benzoic acid N'-isopropyl-hydrazide (71 mg, 0.40 mmoles) in DMF (4 mL) was treated with triethylamine (0.16 mL, 1.19 mmoles), HOBT (64 mg, 0.48 mmoles) and EDCI (91 mg, 0.48 mmol) at room temperature for 48 h. The reaction mixture was partitioned between 1N HCl and ethyl acetate. The organic layer was washed successively with water, 1N NaOH and brine, then dried over sodium sulfate, filtered and concentrated. The crude was absorbed on silica and purified on a silica gel column with a 20-50% ethyl acetate/hexanes gradient to afford the product as a solid (30 mg, 18%). LC-MS m/e 403.49(M+H$^+$)

Example 31

2-(2-methoxy-ethoxy)-benzoic acid N'-[3-(2',3'-dimethyl-biphenyl-2-yl)-propionyl]-N'-isopropyl-hydrazide

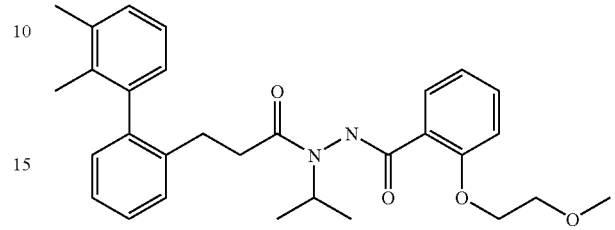

A solution of 3-(2',3'-dimethyl-biphenyl-2-yl)-propionic acid (110 mg, 0.44 mmoles) and 2-(2-methoxy-ethoxy)-benzoic acid-N'-isopropyl hydrazide (100 mg, 0.40 mmoles) in DMF (3 mL) was treated with triethylamine (0.16 mL, 1.19 mmoles), HOBT (64 mg, 0.48 mmoles) and EDCI (91 mg, 0.48 mmoles) at room temperature for 48 h. The reaction mixture was partitioned between 1N HCl and ethyl acetate. The organic layer was washed successively with water, 1N NaOH and brine, then dried over sodium sulfate, filtered and concentrated. The crude was absorbed on silica and purified on a silica gel column with 10% ethyl acetate/hexanes to afford the product (70 mg, 36%). LC-MS m/e 489.39 (M+H$^+$)

Example 32

4-(2-methoxy-ethoxy)-benzoic acid N'-[3-(2',3'-dimethyl-biphenyl-2-yl)-propionyl]-N'-isopropyl-hydrazide

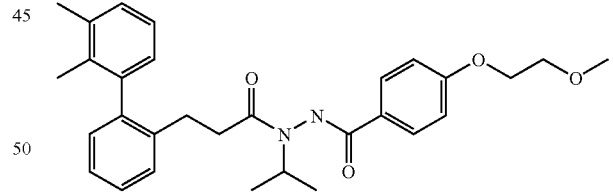

A solution of 3-(2',3'-dimethyl-biphenyl-2-yl)-propionic acid (110 mg, 0.44 mmoles) and 4-(2-methoxy-ethoxy)-benzoic acid-N'-isopropyl hydrazide (100 mg, 0.40 mmoles) in DMF (3 mL) was treated with triethylamine (0.16 mL, 1.19 mmoles), HOBT (64 mg, 0.48 mmoles) and EDCI (91 mg, 0.48 mmoles) at room temperature for 48 h. The reaction mixture was partitioned between 1N HCl and ethyl acetate. The organic layer was washed successively with water, 1N NaOH and brine, then dried over sodium sulfate, filtered and concentrated. The crude was absorbed on silica and purified on a silica gel column with 10% ethyl acetate/hexanes to afford the product (30 mg, 16%). LC-MS m/e 489.40 (M+H$^+$)

Example 33

Thiophene-2-carboxylic acid N'-[3-(2',3'-dimethyl-biphenyl-2-yl)-propionyl]-N'-isopropyl-hydrazide

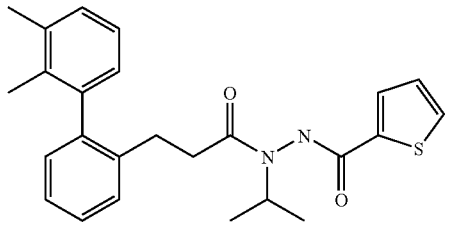

A solution of 3-(2',3'-dimethyl-biphenyl-2-yl)-propionic acid (207 mg, 0.81 mmoles) and thiophene-2-carboxylic acid N'-isopropyl-hydrazide (150 mg, 0.81 mmoles) in DMF (8 mL) was treated with triethylamine (0.34 mL, 2.44 mmoles), HOBT (132 mg, 0.98 mmoles) and EDCI (156 mg, 0.98 mmoles) at room temperature for 48 h. The reaction mixture was partitioned between 1N HCl and dichloromethane. The organic layer was washed successively with 1N NaOH and brine, then dried over sodium sulfate, filtered and concentrated. The crude was absorbed on silica and purified on a silica gel column with a 20-50% ethyl acetate/hexanes gradient to afford the product (173 mg, 51%). LC-MS m/e 421.46 (M+H$^+$)

Example 34

Thiophene-3-carboxylic acid N'-[3-(2',3'-dimethyl-biphenyl-2-yl)-propionyl]-N'-isopropyl-hydrazide

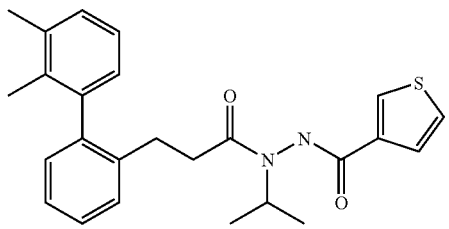

A solution of 3-(2',3'-dimethyl-biphenyl-2-yl)-propionic acid (207 mg, 0.81 mmoles) and thiophene-3-carboxylic acid N'-isopropyl-hydrazide (150 mg, 0.81 mmoles) in DMF (8 mL) was treated with triethylamine (0.34 mL, 2.44 mmoles), HOBT (132 mg, 0.98 mmoles) and EDCI (156 mg, 0.98 mmoles) at room temperature for 48 h. The reaction mixture was partitioned between 1N HCl and dichloromethane. The organic layer was washed successively with 1N NaOH and brine, then dried over sodium sulfate, filtered and concentrated. The crude was absorbed on silica and purified on a silica gel column with a 20-50% ethyl acetate/hexanes gradient to afford the product (172 mg, 50%). LC-MS m/e 421.46 (M+H$^+$)

Example 35

Furan-2-carboxylic acid N'-[3-(2',3'-dimethyl-biphenyl-2-yl)-propionyl]-N'-isopropyl-hydrazide

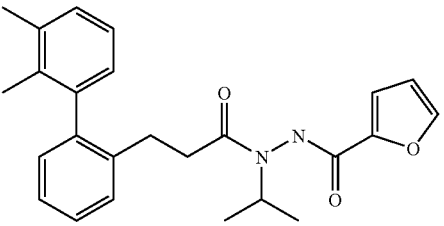

A solution of 3-(2',3'-dimethyl-biphenyl-2-yl)-propionic acid (227 mg, 0.89 mmoles) and furan-2-carboxylic acid N'-isopropyl-hydrazide (150 mg, 0.89 mmoles) in DMF (8 mL) was treated with triethylamine (0.37 mL, 2.67 mmoles), HOBT (144 mg, 1.07 mmoles) and EDCI (205 mg, 1.07 mmoles) at room temperature for 48 h. The reaction mixture was partitioned between 1N HCl and dichloromethane. The organic layer was washed successively with 1N NaOH and brine, then dried over sodium sulfate, filtered and concentrated. The crude was absorbed on silica and purified on a silica gel column with a 20-50% ethyl acetate/hexanes gradient to afford the product (193 mg, 54%). LC-MS m/e 405.46 (M+H$^+$)

Example 36

Furan-3-carboxylic acid N'-[3-(2',3'-dimethyl-biphenyl-2-yl)-propionyl]-N'-isopropyl-hydrazide

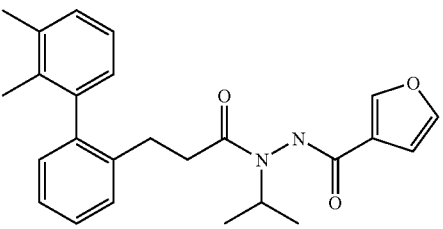

A solution of 3-(2',3'-dimethyl-biphenyl-2-yl)-propionic acid (227 mg, 0.89 mmoles) and furan-3-carboxylic acid N'-isopropyl-hydrazide (150 mg, 0.89 mmoles) in DMF (8 mL) was treated with triethylamine (0.37 mL, 2.67 mmoles), HOBT (144 mg, 1.07 mmoles) and EDCI (205 mg, 1.07 mmoles) at room temperature for 48 h. The reaction mixture was partitioned between 1N HCl and dichloromethane. The organic layer was washed successively with 1N NaOH and brine, then dried over sodium sulfate, filtered and concentrated. The crude was absorbed on silica and purified on a silica gel column with a 20-50% ethyl acetate/hexanes gradient to afford the product (149 mg, 41%). LC-MS m/e 405.52 (M+H$^+$)

Example 37

Isonicotinic acid N'-[3-(2',3'-dimethyl-biphenyl-2-yl)-propionyl]-N'-isopropyl-hydrazide

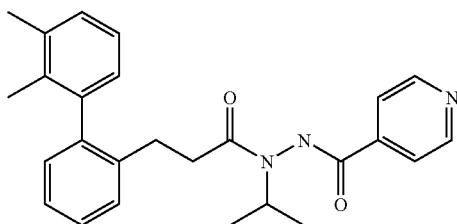

A solution of 3-(2',3'-dimethyl-biphenyl-2-yl)-propionic acid (127 mg, 0.50 mmoles) and isonicotinic acid N'-isopropyl-hydrazyde (ACROS) (167 mg, 0.60 mmoles) in DMF (5 mL) was treated with diisopropylethylamine (0.35 mL, 2.0 mmoles), and PyBroP (350 mg, 0.75 mmoles) at room temperature for 16 h. The reaction mixture was partitioned between 1N NaOH and ethyl acetate. The organic layer was washed with brine, dried over sodium sulfate, filtered and concentrated. The crude was absorbed on silica and purified on a silica gel column with 100% ethyl acetate to afford the product (17 mg, 8%). LC-MS m/e 416.49 (M+H$^+$)

Example 38

Benzoic acid N'-[3-(5-fluoro-2-propoxy-phenyl)-propionyl]-N'-isopropyl-hydrazide

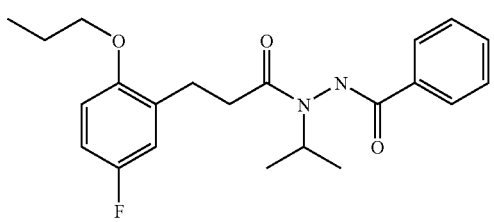

A solution of 3-(5-fluoro-2-propoxy-phenyl)-propionic acid (160 mg, 0.71 mmoles) and benzoic acid N'-isopropyl-hydrazide (106 mg, 0.60 mmoles) in DMF (3 mL) was treated with diisopropylethylamine (0.26 mL, 1.49 mmoles), and PyBroP (416 mg, 0.89 mmoles) at room temperature for 16 h. The reaction mixture was partitioned between 1N HCl and ethyl acetate. The organic layer was washed successively with saturated aqueous sodium bicarbonate and brine, then dried over sodium sulfate, filtered and concentrated. The crude was absorbed on silica and purified on a silica gel column with a 20-50% ethyl acetate/hexanes gradient to afford the product as a solid (84 mg, 30%). LC-MS m/e 387.26 (M+H$^+$)

Example 39

Benzoic acid N'-[3-(2-butoxy-5-fluoro-phenyl)-propionyl]-N'-isopropyl-hydrazide

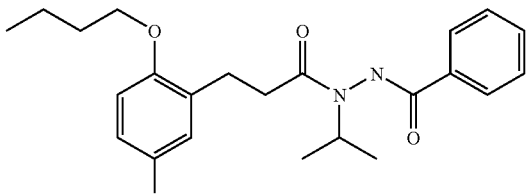

A solution of 3-(2-butoxy-5-fluoro-phenyl)-propionic acid (300 mg, 1.37 mmoles) and benzoic acid N'-isopropyl-hydrazide (203 mg, 1.14 mmoles) in DMF (3 mL) was treated with diisopropylethylamine (0.50 mL, 2.85 mmoles), and PyBroP (800 mg, 1.71 mmoles) at room temperature for 16 h. The reaction mixture was partitioned between 1N HCl and ethyl acetate. The organic layer was washed successively with saturated aqueous sodium bicarbonate and brine, then dried over sodium sulfate, filtered and concentrated. The crude was absorbed on silica and purified on a silica gel column with a 20-40% ethyl acetate/hexanes gradient to afford the product as a solid (20 mg, 5%). LC-MS m/e 401.28 (M+H$^+$)

Example 40

Benzoic acid N'-[3-(2-cyclopentyloxy-5-fluoro-phenyl)-propionyl]-N'-isopropyl-hydrazide

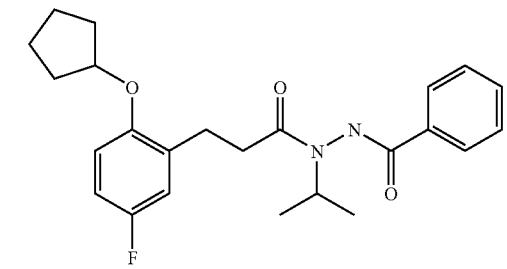

A solution of 3-(2-cyclopentyloxy-5-fluoro-phenyl)-propionic acid (220 mg, 0.87 mmoles) and benzoic acid N'-isopropyl-hydrazide (130 mg, 0.73 mmoles) in DMF (5mL) was treated with diisopropylethylamine (0.32 mL, 1.81 mmoles), and PyBroP (507 mg, 1.09 mmoles) at room temperature for 48 h. The reaction mixture was partitioned between 1N HCl and ethyl acetate. The organic layer was washed successively with saturated aqueous sodium bicarbonate and brine, then dried over sodium sulfate, filtered and concentrated. The crude was absorbed on silica and purified on a silica gel column with a 20-40% ethyl acetate/hexanes gradient to afford the product as a solid (90 mg, 30%). LC-MS m/e 413.32 (M+H$^+$)

Example 41

Benzoic acid N'-[3-(2-cyclobutylmethoxy-5-fluoro-phenyl)-propionyl]-N'-isopropyl-hydrazide

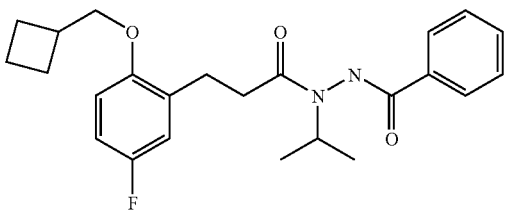

A solution of 3-(2-cyclobutylmethoxy-5-fluoro-phenyl)-propionic acid (195 mg, 0.77 mmoles) and benzoic acid N'-isopropyl-hydrazide (115 mg, 0.64 mmoles) in DMF (5 mL) was treated with diisopropylethylamine (0.28 mL, 1.61 mmoles), and PyBroP (450 mg, 0.97 mmoles) at room temperature for 48 h. The reaction mixture was partitioned between 1N HCl and ethyl acetate. The organic layer was washed successively with saturated aqueous sodium bicarbonate and brine, then dried over sodium sulfate, filtered and concentrated. The crude was absorbed on silica and purified on a silica gel column with a 20-40% ethyl acetate/hexanes gradient to afford the product as a solid (45 mg, 14%). LC-MS m/e 413.32(M+H$^+$)

Example 42

Benzoic acid N'-[3-(3-bromo-phenyl)-propionyl]-N'-isopropyl-hydrazide

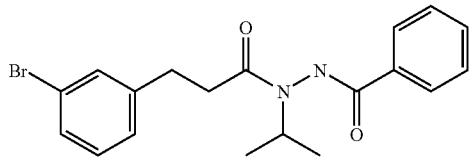

A solution of (3-(3-bromophenyl)propionic acid (257 mg, 1.12 mmoles) and benzoic acid N'-isopropyl-hydrazide (200 mg, 1.12 mmoles) in DMF (6 mL) was treated with triethylamine (0.47 mL, 3.36 mmoles), HOBT (182 mg, 1.34 mmoles) and EDCI (2.58 mg, 1.34 mmoles) at room temperature for 18 h. The reaction mixture was partitioned between water and dichloromethane. The organic layer was washed with brine, dried over sodium sulfate, filtered and concentrated. The crude was absorbed on silica and purified on a silica gel column with a 20-40% ethyl acetate/hexanes gradient to afford the product as a solid (293 mg, 67%).

Example 43

DGAT Phospholipid FlashPlate Assay

Materials for the assay were: PL-FlashPlate: Phospholipid FlashPlates from PerkinElmer, catalog number SMP108; DAG (1,2-Dioleoyl-sn-glycerol) 10 mM suspended in water containing 0.1% Triton X-100; 14C-Pal-CoA (palmitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/ml.

Aqueous buffers were prepared or purchased as follows: The coating buffer (CB) was purchased from PerkinElmer, catalog number SMP900A; the reaction buffer (RB) was 50 mM Tris-HCl, pH 7.5, 100 mM NaCl, 0.01% BSA in water; the washing buffer (WB) is 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 µM with coating buffer (CB). The diluted DAG solution was then added to 384-well PL-FlashPlates at 60 µl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 µM in 100% DMSO. Diluted compound were further diluted 10 fold with reaction buffer (RB). $^{14}$C-Pal-CoA was diluted to 8.3 µM with RB. The DGAT pellet was diluted to 0.13 mg protein/ml with dilution buffer (DB) immediately before it was added to the PL-FlashPlates to start the reaction. 20 µl of the RB-diluted compounds (or 10% DMSO in RB for Total and Blank), 15 µl of RB diluted 14C-Pal-CoA and 15 µl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of IC$_{50}$: The IC$_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

$$(A+((B-A)/(1+((x/C)\hat{\ }D))))$$, with A and B as the bottom and top of the curve (highest and lowest inhibition), respectively, and C as IC$_{50}$ and D as Hill Coefficient of the compound. The results are summarized in Table 1 below:

TABLE 1

| Compound of Example | Activity in DGAT Phospholipid FlashPlate Assay (A = IC$_{50}$ < 0.3 µM, B = IC$_{50}$ < 1 µM) |
|---|---|
| 1 | A |
| 2 | A |
| 3 | A |
| 4 | B |
| 5 | A |
| 6 | A |
| 7 | A |
| 8 | A |
| 9 | A |
| 10 | A |
| 11 | A |
| 12 | B |
| 13 | A |
| 14 | A |
| 15 | A |
| 16 | A |
| 17 | A |
| 18 | A |
| 19 | A |
| 20 | A |
| 21 | B |
| 22 | A |
| 23 | A |

TABLE 1-continued

| Compound of Example | Activity in DGAT Phospholipid FlashPlate Assay (A = IC$_{50}$ < 0.3 μM, B = IC$_{50}$ < 1 μM) |
|---|---|
| 24 | A |
| 25 | B |
| 26 | B |
| 27 | B |
| 28 | B |
| 29 | A |
| 30 | A |
| 31 | B |
| 32 | A |
| 33 | A |
| 34 | A |
| 35 | B |
| 36 | B |
| 37 | B |
| 38 | A |
| 39 | A |
| 40 | A |
| 41 | A |
| 42 | B |

It is to be understood that the invention is not limited to the particular embodiments of the invention described above, as variations of the particular embodiments may be made and still fall within the scope of the appended claims.

What is claimed is:

1. A compound of the formula (I):

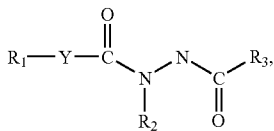

wherein:
Y is (C$_1$-C$_6$) alkyl or (C$_1$-C$_6$) alkyl substituted with aryl;
R$_1$ is substituted or unsubstituted aryl or

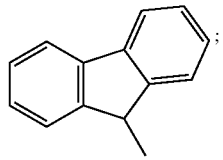

R$_2$ is (C$_1$-C$_6$) alkyl;
R$_3$ is unsubstituted aryl, substituted aryl with a group independently selected from the group consisting of halogen, (C$_1$-C$_6$) alkyl, and —O(CH$_2$)$_m$OCH$_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocycyl substituted with (C$_1$-C$_6$) alkyl, or substituted or unsubstituted 5-10-membered cycloalkyl ring; and
m is 0, 1, 2 or 3,
and pharmaceutically acceptable salts thereof.

2. The compound according to claim 1, wherein:
Y is CH═CH, (CH$_2$)$_n$, or —CH(Ar)CH$_2$; and
n is 1 or 2.

3. The compound according to claim 1, wherein:
R$_1$ is

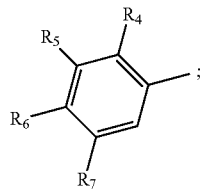

R$_4$ is H, (C$_1$-C$_6$) alkyl, unsubstituted aryl, aryl which is mono-, di- or tri-substituted with a group independently selected from the group consisting of halogen, (C$_1$-C$_6$) alkyl, (C$_1$-C$_6$) alkoxy, —O(CH)(CH$_3$)$_2$, —CF$_3$, —O(CH$_2$)$_m$CH$_3$, —OCF$_3$, —SCH$_3$, —CH(CH$_3$)$_2$, —CN, —SO$_2$CH$_3$, —NO$_2$, and —(CH)$_2$Ar, O-phenyl, —O(CH$_2$)$_m$CH$_3$, or unsubstituted or substituted 4-10 membered cycloalkyl ring attached to the aryl ring by oxygen;
R$_5$, R$_6$, R$_7$ independently of each other are H, halogen, phenyl or (C$_1$-C$_6$) alkyl; and
m is 0, 1, 2 or 3,
and pharmaceutically acceptable salts thereof.

4. The compound according to claim 1, wherein R$_2$ is a cyclomethoxy or cyclobutylmethoxy group.

5. The compound according to claim 1, wherein R$_1$ and R$_3$, independently of each other, are phenyl.

6. The compound according to claim 1, wherein the compound is benzoic acid N'-isopropyl-N'-[3-(3'-methoxy-biphenyl-2-yl)-propionyl]-hydrazide.

7. The compound according to claim 1, wherein the compound is benzoic acid N'-[3-(2-cyclopentyloxy-5-fluoro-phenyl)-propionyl]-N'-isopropyl-hydrazide.

8. The compound according to claim 1, wherein the compound is benzoic acid N'-[3-(3'-chloro-4'-fluoro-biphenyl-2-yl)-propionyl]-N'-isopropyl-hydrazide.

9. The compound according to claim 1, wherein the compound is benzoic acid N'-[3-(2'-chloro-biphenyl-2-yl)-propionyl]-N'-isopropyl-hydrazide.

10. The compound according to claim 1, wherein the compound is benzoic acid N'-[3-(2',5'-dimethyl-biphenyl-2-yl)-propionyl]-N'-isopropyl-hydrazide.

11. The compound according to claim 1, wherein the compound is benzoic acid N'-[3-(2-butoxy-5-fluoro-phenyl)-propionyl]-N'-isopropyl-hydrazide.

12. The compound according to claim 1, wherein the compound is benzoic acid N'-[3-(5'-isopropyl-2'-methoxy-biphenyl-2-yl)-propionyl]-N'-isopropyl-hydrazide.

13. The compound according to claim 1, wherein the compound is benzoic acid N'-[3-(2',3'-dimethyl-biphenyl-2-yl)-acryloyl]-N'-isopropyl-hydrazide.

14. The compound according to claim 1, wherein the compound is benzoic acid N'-[3-(2',3'-dimethyl-biphenyl-2-yl)-propionyl]-N'-isopropyl-hydrazide.

15. The compound according to claim 1, wherein the compound is benzoic acid N'-[3-(2-cyclobutylmethoxy-5-fluoro-phenyl)-propionyl]-N'-isopropyl-hydrazide.

16. A method for the treatment of obesity, type II diabetes or metabolic syndrome in a patient in need thereof, which comprises administering to said patient a therapeutically effective amount of a compound of the formula (I):

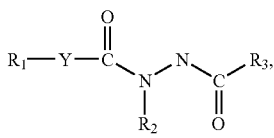

wherein:

Y is $(C_1-C_6)$ alkylene or $(C_1-C_6)$ alkylene substituted with aryl;

$R_1$ is substituted or unsubstituted aryl or

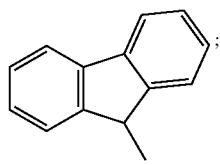

$R_2$ is $(C_1-C_6)$ alkyl;

$R_3$ is unsubstituted aryl, substituted aryl with a group independently selected from the group consisting of halogen, $(C_1-C_6)$ alkyl, and —$O(CH_2)_mOCH_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocycyl substituted with $(C_1-C_6)$ alkyl, or substituted or unsubstituted 5-10-membered cycloalkyl ring; and m is 0, 1, 2 or 3, and pharmaceutically acceptable salts thereof.

17. The method according to claim 16, wherein $R_1$ is

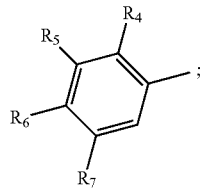

$R_4$ is H, $(C_1-C_6)$ alkyl, unsubstituted aryl, aryl which is mono-, di- or tri-substituted with a group independently selected from the group consisting of halogen, $(C_1-C_6)$ alkyl, $(C_1-C_6)$ alkoxy, —$O(CH)(CH_3)_2$, —$CF_3$, —$O(CH_2)_mCH_3$, —$OCF_3$, —$SCH_3$, —$CH(CH_3)_2$, —CN, —$SO_2CH_3$, —$NO_2$, and —$(CH)_2Ar$, O-phenyl, —$O(CH_2)_mCH_3$, or unsubstituted or substituted 4-10 membered cycloalkyl ring attached to the aryl ring by oxygen;

$R_5$, $R_6$, $R_7$ independently of each other are H, halogen, phenyl or $(C_1-C_6)$ alkyl; and m is 0, 1, 2 or 3, and pharmaceutically acceptable salts thereof.

18. The method according to claim 14, wherein said therapeutically effective amount of said compound is from about 10 mg to about 1000 mg per day.

19. A pharmaceutical composition comprising a therapeutically effective amount of a compound or a pharmaceutically acceptable salt or ester thereof according to claim 1, and a pharmaceutically acceptable carrier.

\* \* \* \* \*